US 6,730,038 B2

(12) United States Patent
Gallant et al.

(10) Patent No.: US 6,730,038 B2
(45) Date of Patent: May 4, 2004

(54) METHOD AND APPARATUS FOR NON-INVASIVELY MEASURING HEMODYNAMIC PARAMETERS USING PARAMETRICS

(75) Inventors: Stuart L. Gallant, San Diego, CA (US); Gregory L. Voss, Solana Beach, CA (US)

(73) Assignee: Tensys Medical, Inc., San Diego, CA (US)

( * ) Notice: Subject to any disclaimer, the term of this patent is extended or adjusted under 35 U.S.C. 154(b) by 187 days.

(21) Appl. No.: 10/072,508

(22) Filed: Feb. 5, 2002

(65) Prior Publication Data

US 2003/0149369 A1 Aug. 7, 2003

(51) Int. Cl.[7] .................................................. A01B 5/02
(52) U.S. Cl. ........................ 600/485; 600/500; 600/503
(58) Field of Search ................................. 600/485, 490, 600/481, 483, 500, 501, 502, 503

(56) References Cited

U.S. PATENT DOCUMENTS

| 4,109,647 A | 8/1978 | Stern et al. |
| 4,127,114 A | 11/1978 | Bretscher |
| 4,154,231 A | 5/1979 | Russell |
| 4,239,047 A | 12/1980 | Griggs, III et al. |
| 4,249,540 A | 2/1981 | Koyama et al. |
| 4,349,034 A | 9/1982 | Ramsey, III |
| 4,476,875 A | 10/1984 | Nilsson et al. |
| 4,566,462 A | 1/1986 | Janssen |

(List continued on next page.)

FOREIGN PATENT DOCUMENTS

| EP | 284 095 B1 | 3/1988 |
| EP | 0 342 249 A1 | 5/1988 |

(List continued on next page.)

OTHER PUBLICATIONS

Carson, E. R., et al. (1983) "The Mathematical Modeling of Metabolic and Endocrine Systems: Model Formulation, Identification, and Validation," John Wiley & Sons, NY, pp. 185–189.

Computerized Screening, Inc. (CSI) Celebrates 25 Years as Visionary Pioneer in Preventive Screening Technology Article by KNB Communications, posted on Friday, May 2, 2003 (2 pages).

(List continued on next page.)

Primary Examiner—Max F. Hindenburg
Assistant Examiner—Navin Natnithithadha
(74) Attorney, Agent, or Firm—Gazdzinski & Associates

(57) ABSTRACT

An improved method and apparatus for non-invasively assessing one or more hemodynamic parameters associated with the circulatory system of a living organism. In one aspect, the invention comprises a method of measuring a hemodynamic parameter (e.g., arterial blood pressure) by applanating or compressing portions of tissue proximate to the blood vessel of concern until a desired condition is achieved, and then measuring the hemodynamic parameter. Such applanation effectively mitigates transfer and other losses created by the tissue proximate to the blood vessel, thereby facilitating accurate and robust tonometric measurement. An algorithm adapted to maintain optimal levels of applanation is also described. Methods and apparatus for scaling such hemodynamic parameter measurements based on subject physiology, and providing treatment to the subject based on the measured parameters, are also disclosed.

43 Claims, 31 Drawing Sheets

U.S. PATENT DOCUMENTS

| | | |
|---|---|---|
| 4,590,948 A | 5/1986 | Nilsson |
| 4,596,254 A | 6/1986 | Adrian et al. |
| 4,651,747 A | 3/1987 | Link |
| 4,664,126 A | 5/1987 | Link |
| 4,719,923 A | 1/1988 | Hartwell et al. |
| 4,754,761 A | 7/1988 | Ramsey, III et al. |
| 4,771,792 A | 9/1988 | Seale |
| 4,796,184 A | 1/1989 | Bahr et al. |
| 4,867,170 A | 9/1989 | Takahashi |
| 4,869,261 A | 9/1989 | Penaz |
| 4,880,013 A | 11/1989 | Chio |
| 4,901,733 A | 2/1990 | Kaida et al. |
| 4,924,871 A | 5/1990 | Honeyager |
| 4,960,128 A | 10/1990 | Gordon et al. |
| 5,029,589 A | 7/1991 | Kato |
| 5,030,956 A | 7/1991 | Murphy |
| 5,033,471 A | 7/1991 | Yokoe et al. |
| 5,072,733 A | 12/1991 | Spector et al. |
| 5,094,244 A | 3/1992 | Callahan et al. |
| 5,119,822 A | 6/1992 | Niwa |
| 5,152,297 A | 10/1992 | Meister et al. |
| 5,158,091 A | 10/1992 | Butterfield et al. |
| 5,163,438 A | 11/1992 | Gordon et al. |
| 5,170,796 A | 12/1992 | Kobayashi |
| 5,238,000 A | 8/1993 | Niwa |
| 5,240,007 A | 8/1993 | Pytel et al. |
| 5,241,964 A | 9/1993 | McQuilkin |
| 5,261,412 A * | 11/1993 | Butterfield et al. ......... 600/485 |
| 5,273,046 A | 12/1993 | Butterfield et al. |
| 5,284,150 A | 2/1994 | Butterfield et al. |
| 5,368,039 A | 11/1994 | Moses |
| 5,406,952 A | 4/1995 | Barnes et al. |
| 5,439,001 A | 8/1995 | Butterfield et al. |
| 5,450,852 A | 9/1995 | Archibald et al. |
| 5,467,771 A | 11/1995 | Narimatsu et al. |
| 5,479,928 A | 1/1996 | Cathignol et al. |
| 5,494,043 A | 2/1996 | O'Sullivan et al. |
| 5,533,511 A | 7/1996 | Kaspari et al. |
| 5,551,440 A | 9/1996 | Miyawaki |
| 5,590,649 A | 1/1997 | Caro et al. |
| 5,617,867 A | 4/1997 | Butterfield et al. |
| 5,634,467 A | 6/1997 | Nevo |
| 5,640,964 A | 6/1997 | Archibald et al. |
| 5,642,733 A | 7/1997 | Archibald et al. |
| 5,649,542 A | 7/1997 | Archibald et al. |
| 5,649,543 A | 7/1997 | Hosaka |
| 5,720,292 A | 2/1998 | Poliac |
| 5,722,414 A | 3/1998 | Archibald et al. |
| 5,738,103 A | 4/1998 | Poliac |
| 5,797,850 A | 8/1998 | Archibald et al. |
| 5,832,924 A | 11/1998 | Archibald et al. |
| 5,833,618 A | 11/1998 | Caro et al. |
| 5,848,970 A | 12/1998 | Voss et al. |
| 5,876,346 A | 3/1999 | Corso |
| 5,882,311 A | 3/1999 | O'Rourke |
| 5,895,359 A | 4/1999 | Peel, III |
| 5,908,027 A | 6/1999 | Butterfield et al. |
| 5,916,180 A | 6/1999 | Cundari et al. |
| 5,938,618 A | 8/1999 | Archibald et al. |
| 5,941,828 A | 8/1999 | Archibald et al. |
| 5,964,711 A | 10/1999 | Voss et al. |
| 5,993,394 A | 11/1999 | Poliac |
| 6,010,457 A | 1/2000 | O'Rourke |
| 6,017,314 A | 1/2000 | Poliac |
| 6,027,452 A | 2/2000 | Flaherty et al. |
| 6,099,477 A | 8/2000 | Archibald et al. |
| 6,132,382 A | 10/2000 | Archibald et al. |
| 6,159,157 A | 12/2000 | Archibald et al. |
| 6,176,831 B1 | 1/2001 | Voss et al. |
| 6,228,033 B1 | 5/2001 | Koobi et al. |
| 6,228,034 B1 | 5/2001 | Voss et al. |
| 6,231,517 B1 | 5/2001 | Forstner |
| 6,241,679 B1 | 6/2001 | Curran |
| 6,245,022 B1 | 6/2001 | Archibald et al. |
| 6,270,461 B1 | 8/2001 | Chio |
| 6,340,349 B1 | 1/2002 | Archibald et al. |
| 6,371,921 B1 | 4/2002 | Caro et al. |
| 6,471,655 B1 | 10/2002 | Baura |
| 6,514,211 B1 * | 2/2003 | Baura ........................ 600/490 |
| 6,554,774 B1 | 4/2003 | Miele |
| 6,558,335 B1 | 5/2003 | Thede |

FOREIGN PATENT DOCUMENTS

| | | |
|---|---|---|
| EP | 0595 666 B1 | 9/1993 |
| EP | 0 603 666 A2 | 12/1993 |
| EP | 0818 176 A | 7/1996 |
| WO | WO 84 00290 | 2/1984 |
| WO | WO 92/07508 | 10/1991 |
| WO | WO 95 13014 | 5/1995 |
| WO | WO 98 25511 A | 6/1998 |

OTHER PUBLICATIONS

SQU Journal of Medical Sciences Article re Non–dipping Blood Pressure in Normotensive Patients with Obstructive Sleep Apnea by Bazdawi Al–Riyami, Hussain S. Al–Khatim and Mohammad O Hassan (1 page).

Noninvasive Cardiovascular Monitoring (CircMon) information by JR Medical Ltd. (5 pages).

Drzewiecki, G. (1995) "Noninvasive Assessment of Arterial Blood Pressure and Mechanics," The Biomedical Engineering Handbook CRC Press, Boca Raton, FL, pp. 1196–1211.

Hartley, C.J., et al. (1991) "An Ultrasonic Method for Measuring Tissue Displacement: Technical Details and Validation for Measuring Myocardial Thickening," IEEE Trans Biomed, 38:735–747.

Cariou, Alain, et al. (1998) "Noninvasive Cardiac Output Monitoring by Aortic Blood Flow Determination: Evaluation of the Sometec Cynemo–3000 System," Critical Care Medicine, vol. 26, No. 12, pp. 2066–2072.

Advertisement for HemoSonic™ 100 by Arrow International—licensed under U.S. Patent 5,479,928 listed above.

Mehra, Mandeep R., et al. (May/Jun. 2000) "Emergence of Electronic Home Monitoring In Chronic Heart Failure: Rationale, Feasibility, and Early Results with the HomMed Sentry–Observer System," (consisting of 3 pages).

Anderson, E.A., et al. (1989) "Flow–Mediated and Reflex Changes in Large Peripheral Artery Tone in Humans," Circulation 79:93–100.

Boashash, B., et al. (1987) "An Efficient Real–Time Implementation of the Wigner–Ville Distribution," IEEE Trans ASSP 35:1611–1618.

Drzewiecki, G.M., et al. (1985) Generalization of the Transmural Pressure–Area Relation for the Femoral Artery, $7^{th}$ Annual IEEE EMBS Conference 507.

Hoeks, A.P.G., et al. (1985) Transcutaneous Detection of Relative Chages in Artery Diameter, Ultrasound in Med and Bio 11:51–59.

* cited by examiner (1 OF 2)

(2 OF 2)

(1 OF 2)

(2 OF 2)

(1 OF 4)

(2 OF 4)

(3 OF 4)

(4 OF 4)

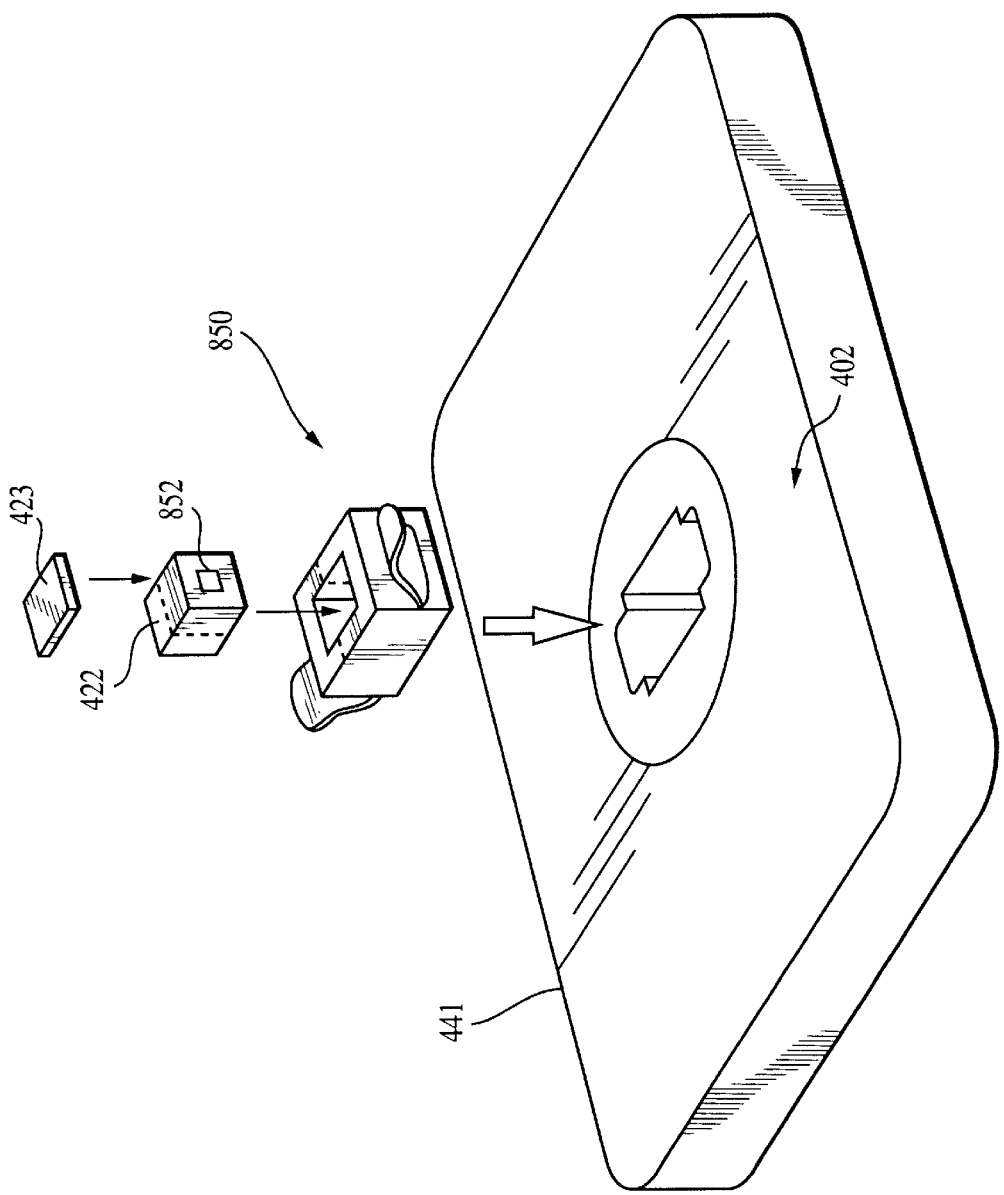

(1 OF 2)

(2 OF 2)

METHOD AND APPARATUS FOR NON-INVASIVELY MEASURING HEMODYNAMIC PARAMETERS USING PARAMETRICS

BACKGROUND OF THE INVENTION

1. Field of the Invention

This invention relates generally to methods and apparatus for monitoring parameters associated with the circulatory system of a living subject, and specifically to the non-invasive monitoring of arterial blood pressure.

2. Description of Related Technology

The accurate, continuous, non-invasive measurement of blood pressure has long been sought by medical science. The availability of such measurement techniques would allow the caregiver to continuously monitor a subject's blood pressure accurately and in repeatable fashion without the use of invasive arterial catheters (commonly known as "A-lines") in any number of settings including, for example, surgical operating rooms where continuous, accurate indications of true blood pressure are often essential.

Several well known techniques have heretofore been used to non-invasively monitor a subject's arterial blood pressure waveform, namely, auscultation, oscillometry, and tonometry. Both the auscultation and oscillometry techniques use a standard inflatable arm cuff that occludes the subject's brachial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, true continuous, beat-to-beat blood pressure monitoring cannot be achieved using these techniques.

Occlusive cuff instruments of the kind described briefly above have generally been somewhat effective in sensing long-term trends in a subject's blood pressure. However, such instruments generally have been ineffective in sensing short-term blood pressure variations, which are of critical importance in many medical applications, including surgery.

The technique of arterial tonometry is also well known in the medical arts. According to the theory of arterial tonometry, the pressure in a superficial artery with sufficient bony support, such as the radial artery, may be accurately recorded during an applanation sweep when the transmural pressure equals zero. The term "applanation" refers to the process of varying the pressure applied to the artery. An applanation sweep refers to a time period during which pressure over the artery is varied from overcompression to undercompression or vice versa. At the onset of a decreasing applanation sweep, the artery is overcompressed into a "dog bone" shape, so that pressure pulses are not recorded. At the end of the sweep, the artery is undercompressed, so that minimum amplitude pressure pulses are recorded. Within the sweep, it is assumed that an applanation occurs during which the arterial wall tension is parallel to the tonometer surface. Here, the arterial pressure is perpendicular to the surface and is the only stress detected by the tonometer sensor. At this pressure, it is assumed that the maximum peak-to-peak amplitude (the "maximum pulsatile") pressure obtained corresponds to zero transmural pressure.

One prior art device for implementing the tonometry technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to at least some of the transducers. An array of different transducers is used to ensure that at least one transducer is always over the artery, regardless of array position on the subject. This type of tonometer, however, is subject to several drawbacks. First, the array of discrete transducers generally is not anatomically compatible with the continuous contours of the subject's tissue overlying the artery being sensed. This has historically led to inaccuracies in the resulting transducer signals. In addition, in some cases, this incompatibility can cause tissue injury and nerve damage and can restrict blood flow to distal tissue.

Other prior art techniques have sought to more accurately place a single tonometric sensor laterally above the artery, thereby more completely coupling the sensor to the pressure variations within the artery. However, such systems may place the sensor at a location where it is geometrically "centered" but not optimally positioned for signal coupling, and further typically require comparatively frequent re-calibration or repositioning due to movement of the subject during measurement.

Tonometry systems are also commonly quite sensitive to the orientation of the pressure transducer on the subject being monitored. Specifically, such systems show a degradation in accuracy when the angular relationship between the transducer and the artery is varied from an "optimal" incidence angle. This is an important consideration, since no two measurements are likely to have the device placed or maintained at precisely the same angle with respect to the artery. Many of the foregoing approaches similarly suffer from not being able to maintain a constant angular relationship with the artery regardless of lateral position, due in many cases to positioning mechanisms which are not adapted to account for the anatomic features of the subject, such as curvature of the wrist surface.

Another significant drawback to arterial tonometry systems in general is their inability to continuously monitor and adjust the level of arterial wall compression to an optimum level. Generally, optimization of arterial wall compression has been achieved only by periodic recalibration. This has required an interruption of the subject monitoring function, which sometimes can occur during critical periods. This disability severely limits acceptance of tonometers in the clinical environment.

One of the most significant limitations of prior art tonometry approaches relates to incomplete pressure pulse transfer from the interior of the blood vessel to the point of measurement on the surface of the skin above the blood vessel. Specifically, even when the optimum level of arterial compression is achieved, there is incomplete and often times complex coupling of the arterial blood pressure through the vessel wall and through the tissue to the surface of the skin, such that the magnitude of pressure variations actually occurring within the blood vessel is somewhat different than that measured by a tonometric sensor (pressure transducer) placed on the skin. Hence, any pressure signal or waveform measured at the skin necessarily differs from the true pressure within the artery. Modeling the physical response of the arterial wall, tissue, musculature, tendons, bone, skin of the wrist is no small feat, and inherently includes uncertainties and anomalies for each separate individual. These uncertainties and anomalies introduce unpredictable error into any measurement of blood pressure made via a tonometric sensor. FIGS. 1 and 2 illustrate the cross-section of a typical human wrist, illustrating the various components and their relationships during normal (uncompressed) and applanated (compressed) states.

FIG. 3 graphically illustrates the foregoing principles, specifically the variability in the tonometric measurements relative to the invasive "A-line" or true arterial pressure. FIG. 3 shows exemplary tonometric pulse pressure (i.e., systolic minus diastolic pressure) data obtained during applanation of the subject's radial artery to the mean pressure. FIG. 3 demonstrates the differences between the pulse pressures measured with the non-invasive prior art tonometric apparatus and the invasive A-Line catheter; note that these differences are generally neither constant nor related to the actual pulse pressure. Hence, there can often be very significant variance in the tonometrically-derived measurements relative to the invasive catheter pressure, such variance not being adequately addressed by prior art techniques.

Based on the foregoing, there is needed an improved methodology and apparatus for accurately, continuously, and non-invasively measuring blood pressure within a living subject. Such improved methodology and apparatus would ideally allow for continuous tonometric measurement of blood pressure which is reflective of true intra-arterial (catheter) pressure, while also providing robustness and repeatability under varying patient physiology and environmental conditions. Such method and apparatus would also be easily utilized by both trained medical personnel and untrained individuals, thereby allowing certain subjects to accurately and reliably conduct self-monitoring.

SUMMARY OF THE INVENTION

The present invention satisfies the aforementioned needs by an improved method and apparatus for non-invasively and continuously assessing hemodynamic properties, including arterial blood pressure, within a living subject.

In a first aspect of the invention, an improved method of obtaining a pressure signal obtained from a blood vessel of a living subject using parametric scaling is disclosed. The method generally comprises applanating a portion of tissue proximate to a blood vessel to achieve a desired condition, and measuring the pressure associated with the blood vessel non-invasively. The measured pressure may then be optionally scaled using parametric data obtained from the subject (or other subjects, for example, on a statistical basis). In one exemplary embodiment of the method, the portion of the tissue (e.g., that proximate to and effectively surrounding the blood vessel of interest) is applanated or compressed to a level which correlates generally to the maximum pulse pressure amplitude for the blood vessel. This greatly minimizes the error between the true intra-vessel pressure and the tonometric reading. The tonometric reading is then optionally scaled (adjusted) for any remaining error based on parametric data comprising the body mass index (BMI) and pulse pressure (PP) for the subject being evaluated. In certain cases, such as those where there is little error or transfer loss resulting from the tissue interposed between the blood vessel wall and tonometric transducer, little or no scaling is needed. In other cases (e.g., where the transfer loss is significant), scaling of the tonometric pressure reading may be appropriate. In one exemplary variant of the method, discrete ranges of parametric data (e.g., BMI/PP) are established such that a given range of data correlates to a unitary (or deterministic) scaling factor or set of factors.

In another exemplary embodiment, a ratio of the BMI to wrist circumference (WC) is formed, and appropriate scaling applied based thereon.

In a second aspect of the invention, an improved apparatus for applanating tissue to provide non-invasive blood pressure measurements is disclosed. The apparatus comprises an applanation element adapted to apply a level of applanation or compression to the tissue proximate to the blood vessel while also measuring pressure tonometrically. In one exemplary embodiment, the applanation element comprises a substantially rectangular pad having an aperture centrally located therein. The aperture is a cylindrical shape having one or more pressure transducers disposed therein and set to a predetermined depth with respect to the contact surface of the pad. A drive mechanism is connected to the element to allow varying levels of force to be applied to the tissue. One or more stepper motors with position encoders are employed to permit precise positioning of the applanation element with respect to the blood vessel/tissue.

In a third aspect of the invention, an improved method for locating the optimal applanation for measuring a hemodynamic parameter is disclosed. The method generally comprises varying the position of the aforementioned applanation element relative to the blood vessel such that varying hemodynamic conditions within the blood vessel are created over time. The optimal level of applanation for the element is then determined by analyzing data obtained tonometrically from the blood vessel (i.e., the overlying tissue), the optimal level subsequently being established to monitor the selected parameter. In one exemplary embodiment, the hemodynamic parameter comprises arterial blood pressure, and the applanation element is varied in position with respect to the blood vessel so as to create a progressively increasing level of compression (so-called "applanation sweep"). The optimal applanation occurs where the highest or maximum pulse pressure is observed. An algorithm is used to iteratively analyze the pressure waveform obtained during the sweep and identify the optimum (maximum pulse pressure) point. The applanation level is then adjusted or "servoed" around that maximal point, where additional measurement and processing occurs. Optionally, the foregoing methodology may be coupled with optimization routines and positional variations associated with one or more other dimensions (e.g., lateral, proximal, and angle of incidence with respect to the normal, for the human radial artery), such that all parameters are optimized, thereby providing the most accurate tonometric reading.

In a fourth aspect of the invention, an improved method for scaling the blood pressure measurements obtained from a living subject is disclosed. The method generally comprises: determining at least one physiologic parameter of the subject; forming a relationship between the at least one parameter and a scaling function; and using the scaling function to scale raw (i.e., unscaled) blood pressure data. In one exemplary embodiment, the blood pressure measurements are obtained from the radial artery of the subject, and two physiologic parameters are utilized: the first parameter comprises the body mass index (BMI) of the subject, and the second parameter the tonometrically measured pulse pressure (PP). An index or ratio of the BMI to the PP is then formed. This index is compared to a predetermined set of criteria relating the index value to the required scaling factor to be applied to the raw blood pressure data. The scaling criteria may be either discrete (e.g., multiple index "bands" having a different scaling factor associated therewith) or continuous in nature. The required scaling can be accomplished automatically (such as via a look-up table, algorithm or similar mechanism in the system software), or alternatively manually, such as via a nomograph, graph, or table.

In a second embodiment, the BMI is related to the wrist circumference of the subject as determined from the subject. In yet another embodiment, the body fat content of the subject is used to develop a scaling function.

In a fifth aspect of the invention, an improved computer program for implementing the aforementioned methods is disclosed. In one exemplary embodiment, the computer program comprises an object code representation of a C++ source code listing, the object code representation being disposed in the program memory or similar storage device of a microcomputer system. The program is adapted to run on the microprocessor of the microcomputer system. One or more subroutines for implementing the applanation optimization and scaling methodologies described above are included within the program. In a second exemplary embodiment, the computer program comprises an instruction set disposed within the storage device (such as the embedded program memory) of a digital processor.

In a sixth aspect of the invention, an improved non-invasive system for assessing one or more hemodynamic parameters is disclosed. The system includes the aforementioned applanation apparatus, along with a digital processor and storage device. In one exemplary embodiment, the apparatus comprises a pressure transducer disposed in the applanation element which is used to applanate the radial artery of a human. The processor is operatively connected to the pressure transducer and applanation apparatus, and facilitates processing signals from the pressure transducer during blood pressure measurement, as well as control of the applanation mechanism (via a microcontroller). The processor further includes a program memory (such as an embedded flash memory) with the aforementioned algorithm stored therein in the form of a computer program. The storage device is also coupled to the processor, and allows for storage of data generated by the pressure transducer and/or processor during operation. In one exemplary variant, the apparatus further includes a second storage device (e.g., EEPROM) which is associated with the transducer and removably coupled to the apparatus, such that the transducer and EEPROM may be easily swapped out by the user. The removable transducer/EEPROM assembly is pre-configured with given scaling data which is particularly adapted for subjects having certain parametrics (e.g., BMI within a certain range). In this fashion, the user simply evaluates the parametrics, and selects the appropriate assembly for use with the apparatus. The apparatus supplies an appropriate value of PP (e.g., a "corrected" value derived from recently obtained data), thereby generating the BMI/PP ratio needed to enter the scaling function (e.g., lookup table). Once the appropriate scaling factor is selected, it is automatically applied to the unscaled pressure waveform. No other calibration or scaling is required, thereby substantially simplifying operation of the apparatus while allowing for highly accurate and continuous pressure readings.

In another exemplary variant, the second storage device is configured so as to carry a plurality of scaling factors/functions, the appropriate one(s) of which is/are selected at time of use through parametric data supplied to the apparatus.

In an seventh aspect of the invention, an improved method of providing treatment to a subject using the aforementioned methodologies is disclosed. The method generally comprises the steps of: selecting a blood vessel of the subject useful for measuring pressure data; applanating the blood vessel to an optimal level; measuring the pressure data when the blood vessel is optimally applanated; scaling the measured pressure data; and providing treatment to the subject based on this scaled pressure data. In one exemplary embodiment, the blood vessel comprises the radial artery of the human being, and the aforementioned methods of optimally applanating the blood vessel and scaling the pressure waveform using BMI/PP are utilized.

These and other features of the invention will become apparent from the following description of the invention, taken in conjunction with the accompanying drawings.

BRIEF DESCRIPTION OF THE DRAWINGS

FIG. 8a is a side plan view of an exemplary unitary transducer/storage device assembly useful with the apparatus of FIG. 8.

DETAILED DESCRIPTION OF THE INVENTION

Figure 2:
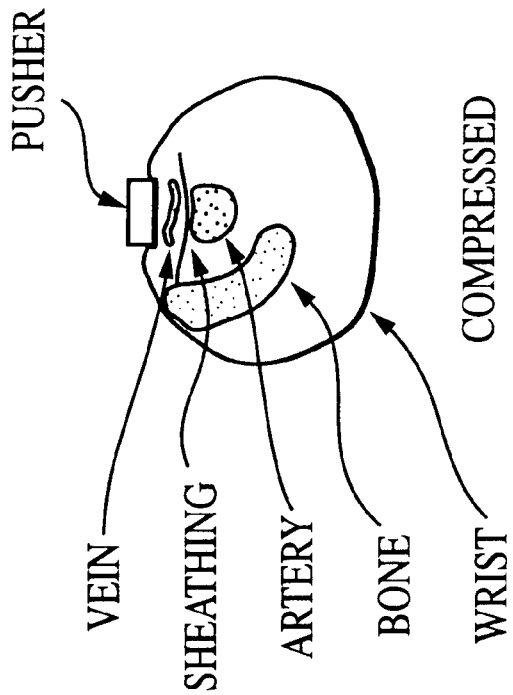
FIG. 2 is a cross-sectional diagram or the wrist area of FIG. 1, illustrating the effect of tonometric applanation on the radial artery and structures.
Figure 1:
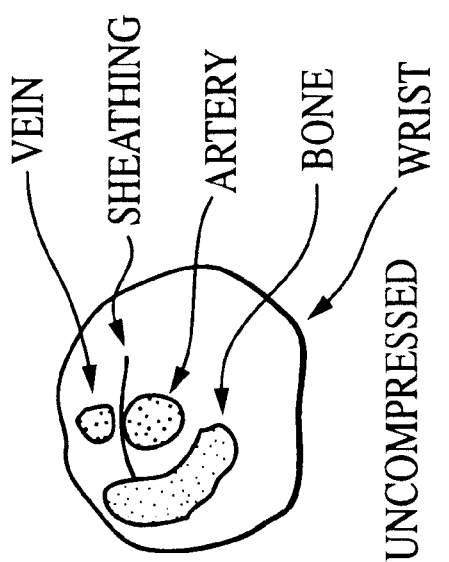
FIG. 1 is a cross-sectional diagram of the wrist area of an exemplary human subject, illustrating the radial artery and other tissue and structures, in an unapplanated (uncompressed) state.
Figure 3:
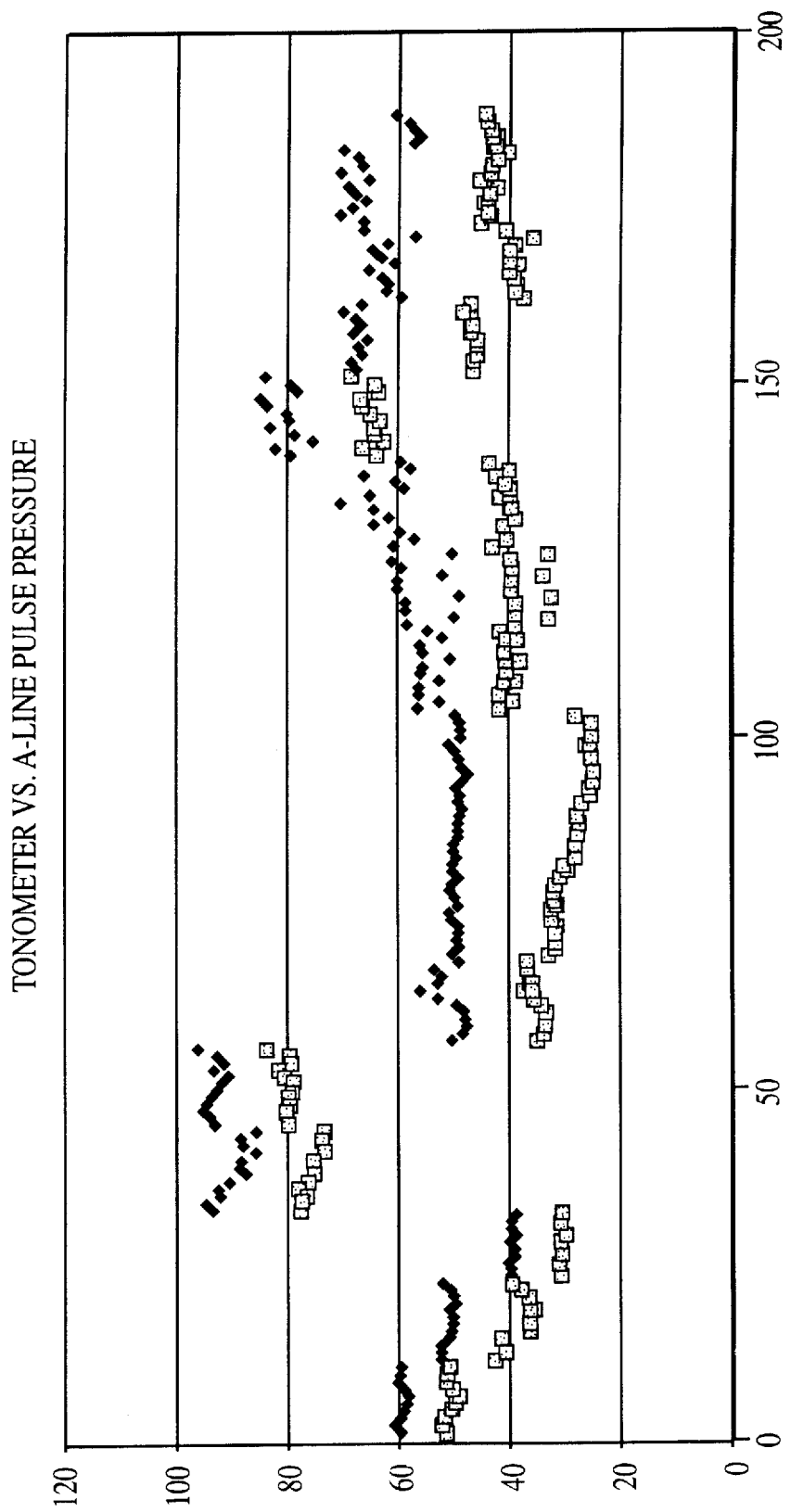
FIG. 3 is a graph illustrating the relationship between the tonometrically obtained pulse pressure and the corresponding invasive catheter (A-line) pulse pressure for a typical human subject when the radial artery is applanated to mean arterial pressure.

Reference is now made to the drawings wherein like numerals refer to like parts throughout.

It is noted that while the invention is described herein primarily in terms of a method and apparatus for assessment of hemodynamic parameters of the circulatory system via the radial artery (i.e., wrist) of a human subject, the invention may also be readily embodied or adapted to monitor such parameters at other blood vessels and locations on the human body, as well as monitoring these parameters on other warm-blooded species. All such adaptations and alternate embodiments are readily implemented by those of ordinary skill in the relevant arts, and are considered to fall within the scope of the claims appended hereto.

As used herein, the term "hemodynamic parameter" is meant to include parameters associated with the circulatory system of the subject, including for example pressure (e.g., diastolic, systolic, pulse, or mean pressure). The term "parameter" or "physiologic parameter" is meant to include measurements or quantities associated with the physiology subject, including for example the subject's weight, height, body mass index (BMI), wrist circumference, ankle circumference, or body fat content, but may also include one or more "hemodynamic" parameters previously defined herein (e.g., blood pressure, etc.).

Additionally, it is noted that the terms "tonometric," "tonometer," and "tonometery" as used herein are intended to broadly refer to non-invasive surface measurement of one or more hemodynamic parameters such as pressure, such as by placing a sensor in communication with the surface of the skin, although contact with the skin need not be direct (e.g., such as through a coupling medium or other interface).

The terms "applanate" and "applanation" as used herein refer to the compression (relative to a state of non-compression) of tissue, blood vessel(s), and other structures such as tendon or muscle of the subject's physiology. Similarly, an applanation "sweep" refers to one or more periods of time during which the applanation level is varied (either increasingly, decreasingly, or any combination thereof). Although generally used in the context of linear (constant velocity) position variations, the term "applanation" as used herein may conceivably take on any variety of other forms, including without limitation (i) a continuous non-linear (e.g., logarithmic) increasing or decreasing compression over time; (ii) a non-continuous or piece-wise continuous linear or non-linear compression; (iii) alternating compression and relaxation; (iv) sinusoidal or triangular waves functions; (v) random motion (such as a "random walk"; or (vi) a deterministic profile. All such forms are considered to be encompassed by the term.

Lastly, the term "digital processor" is meant to include any integrated circuit or other electronic device (or collection of devices) capable of performing an operation on at least one instruction including, without limitation, reduced instruction set core (RISC) processors such as those manufactured by ARM Limited of Cambridge, UK, CISC microprocessors, central processing units (CPUs), and digital signal processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Overview

In one fundamental aspect, the present invention comprises a method of accurately measuring one or more hemodynamic parameters using optimal applanation and scaling of raw or unscaled measurements. In general terms, such applanation mitigates transfer loss and other errors introduced by non-invasive (e.g., tonometric) measurement techniques as applied to the complex system of blood vessels, tissue, muscle, and skin at the location of measurement of the hemodynamic parameter. For example, as will be described in greater detail below, the present invention is useful for accurately measuring the blood pressure using a tonometric or surface pressure sensor disposed over the radial artery of a human being, the measured pressure waveform potentially varying substantially from that actually experienced within the radial artery itself. In one embodiment, a specially configured applanation (compression) apparatus is disclosed, wherein an applanation element is utilized to compress or bias the tissue and accordingly, the blood vessel contained therein. This applanation apparatus advantageously with associated pressure transducer may be used alone as described in detail herein, or in conjunction with literally any type of other apparatus adapted for hemodynamic parameter measurement, including for example the devices described in co-pending U.S. patent application Ser. No. 09/815,982 entitled "Method and Apparatus for the Noninvasive Assessment of Hemodynamic Parameters Including Blood Vessel Location" filed Mar. 22, 2001, and Ser. No. 09/815,080 entitled "Method and Apparatus for Assessing Hemodynamic Parameters within the Circulatory System of a Living Subject" also filed Mar. 22, 2001, both of which are assigned to the assignee hereof and incorporated herein by reference in their entirety.

Since the signal under measurement (e.g. pressure) is time variant, iteration and optimization are selectively utilized within the algorithm embodying the methodology of the present invention to account for this variation. Specifically, the signal is time variant over the short period of the cardiac cycle, over the longer period of the respiratory cycle, and potentially over the even longer or shorter period of hemodynamic changes resulting from varying drug concentrations and volume changes. Accordingly, the algorithm described herein utilizes the aforementioned applanation mechanism to continually find and maintain the optimal level of applanation, thereby maintaining an environment conducive for accurate, continuous, and non-invasive parametric measurement.

It will further be noted that the optimal bias technique of the present invention can be used in conjunction with lateral (transverse), proximal, or other positioning techniques to help locate the pressure transducer(s) over the blood vessel of interest. To this end, any number of different positioning approaches may be employed either alone or in combination (where compatible). For example, the lateral positioning based on analysis of the pressure signal obtained by a tonometric sensor disposed generally over the blood vessel (described subsequently herein) may be utilized. Alternatively, the primarily acoustic lateral positioning and wall detection approaches described in the aforementioned co-pending applications may be used. As yet another alternative, manual location and positioning of the applanators and transducer over the selected blood vessel may be employed.

Applanation Apparatus for Pressure Measurement

Figure 4:
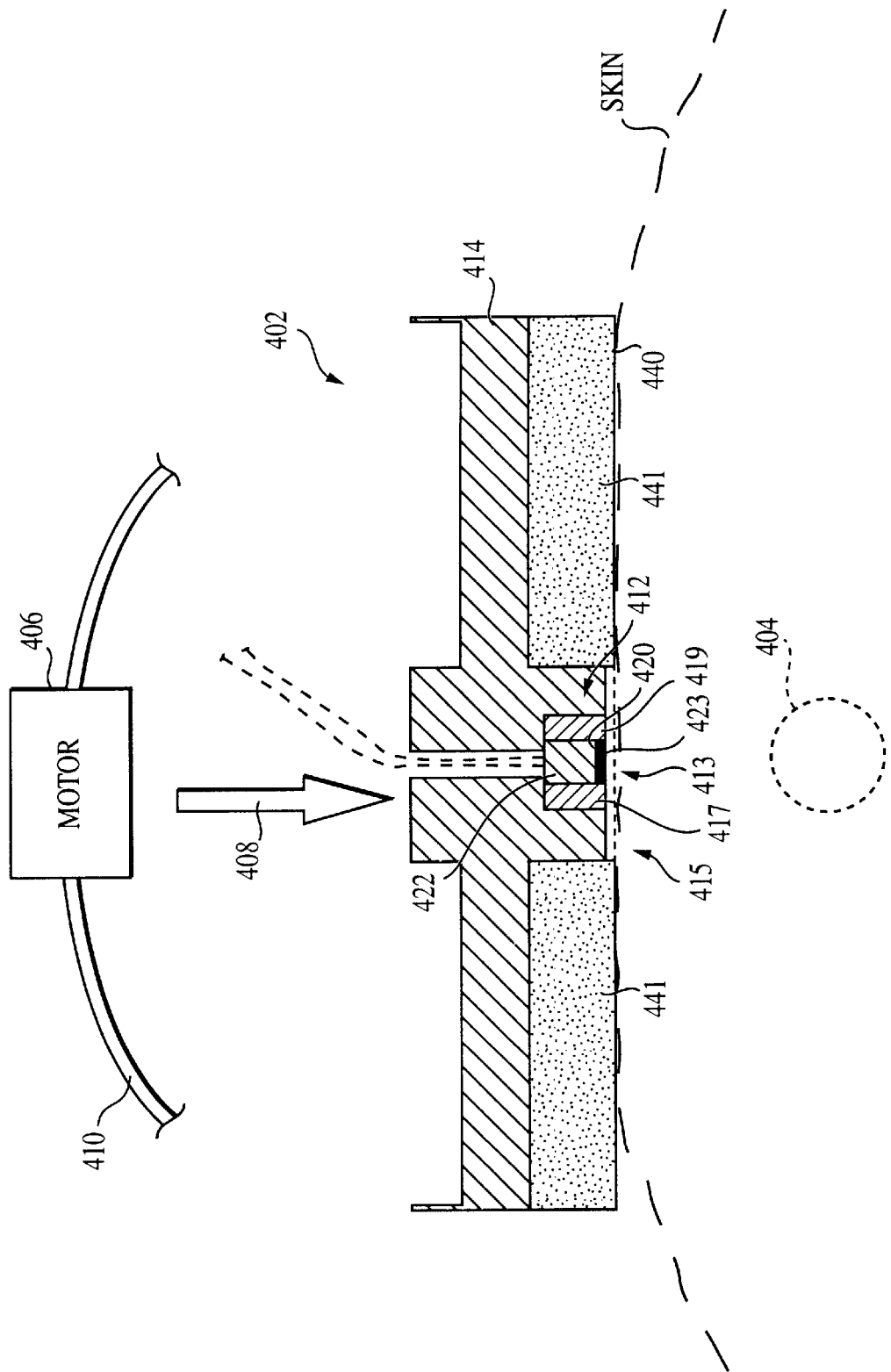
FIG. 4 is a side elevational view of one embodiment of the applanation apparatus of the present invention.
Figure 4A:
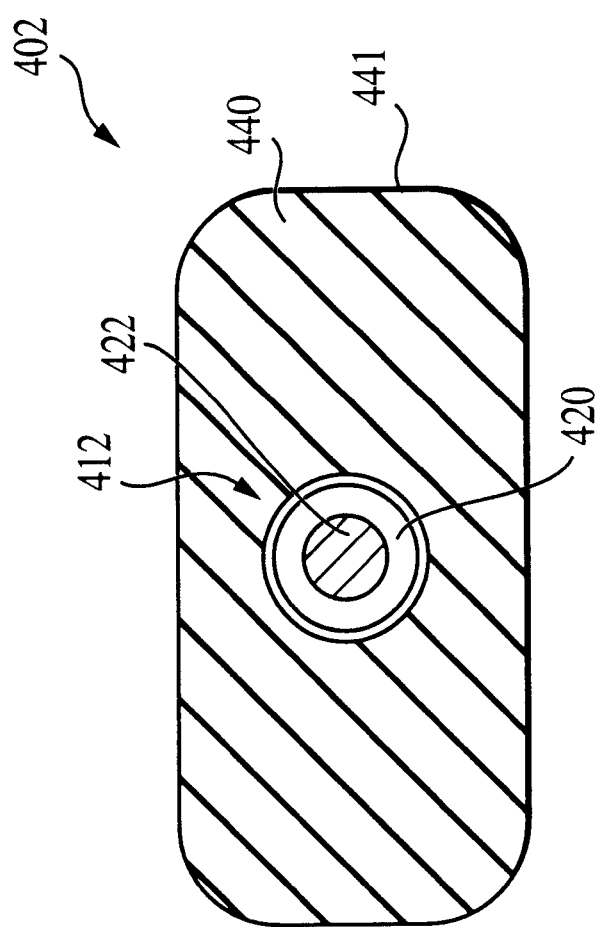
FIG. 4a is a plan view of the contact pad of the apparatus of FIG. 4, illustrating the relationship between applanation element and pressure transducer.

Referring now to FIGS. 4–4a, a first embodiment of the applanation apparatus of the invention is described in detail.

The ability to accurately measure the pressure associated with a blood vessel depends largely upon the mechanical configuration of the applanation mechanism. Under the typical prior art approaches previously discussed, the pressure transducer comprises the applanation mechanism such that the mechanism and transducer are fixed as a single unit. Hence, the pressure transducer experiences the full force applied to deform the tissue, structures, and blood vessel. This approach neglects the component of the applantion force required to compress this interposed tissue, etc. as it relates to the pressure measured tonometrically from the blood vessel. Conversely, under no compression, the magnitude of the pressure within the blood vessel is attenuated or masked by the interposed tissue such that the pressure measured tonometrically is less than that actually existing in the vessel (so-called "transfer loss").

In contrast, the apparatus of the present invention embodies the pressure transducer disposed within an applanation element, the latter having a specially designed configuration adapted to mitigate the effects of such transfer loss in a simple, repeatable, and reliable way such that it can be either (i) ignored or (ii) compensated for as part of the tonometric measurement. As discussed in greater detail below, the shape, size, placement, and selection of materials for the applanation element can be important in determining the amount of transfer loss experienced under a given set of conditions. Specifically, these factors largely dictate the relationship between the maximum pulse pressure and the mean pressure, and hence ultimately the error associated with a given tonometric pressure reading.

As shown in the exemplary embodiment of FIG. 4, the applanation element 402 is used to compress the tissue generally surrounding the blood vessel 404 of interest, and to apply force to the blood vessel wall so as to begin to overcome the wall or hoop stress thereof. The applanation element (or applanator) 402 is coupled to a drive motor 406 which provides the compressive applanating force 408 in reaction to the patient via a wristband or brace 410 (or an external surface). The applanator 402 of the illustrated embodiment includes a generally rectangular applanator body 414 with a substantially cylindrical projection 412 (see FIG. 4a), and a contact pad 441 disposed on the bottom surface thereof. The body 414 is molded from a polymer (e.g., polycarbonate) for ease of manufacturing, rigidity, and low cost, although other materials may be chosen. A substantially cylindrical aperture 415 is formed centrally in the contact pad 441 to receive the body projection 412. Accordingly, when the contact surface 440 of the applanator pad 441 is pressed against the skin of the patient, a generally rectangular contact area ("footprint") with a central aperture results.

A pressure transducer 422, disposed substantially over the blood vessel 404 and received within an aperture 413 of the applanator body 414, is used to obtain tonometric pressure readings from the surface of the skin (tissue) overlying the blood vessel. The height of the active face 420 of the transducer 422 is set within its housing 417 so as to provide the desired degree of coupling between the transducer face and tissue when the applanator 402 is compressed onto the subject's tissue. It will be recognized, however, that the transducer 422 or it's housing 417 may be made adjustable or movable within the aperture 413 so as to facilitate optimal positioning under different operating conditions and/or to accommodate different subject physiologies.

As shown in FIG. 4, a thin polymer layer 423 is also applied over the top of the transducer face 420 so as to (i) couple the transducer face more positively to the tissue; and (ii) level the surface contacting the tissue formed by the transducer face, the body projection 412, and the transducer housing 417. Specifically, a layer of a pliable, compressible silicone based compound (e.g., silicone rubber) is formed over the transducer face 420 within the housing 417 as shown, although other materials may be used. In addition to its superior physical properties and excellent pressure signal coupling from the tissue to the transducer face 420, the silicone layer 423 also allows for some degree of variation in the distance between the transducer face and the top surface 419 of the housing 417 during manufacture, since the silicone is "filled" to the appropriate depth to provide a level and effectively continuous top surface.

The motor 406 of the applanator assembly is, in the present embodiment, rigidly coupled to the wrist brace assembly 410 so as to provide a substantially invariant platform against which the motor may exert reaction force while applanating the subject's tissue. This "rigid" configuration is utilized so as to avoid any significant compliance of the assembly as the motor 406 drives the contact pad 441 in compression of the tissue/blood vessel during applanation. This rigidity is advantageous from the standpoint that helps allow the pressure transducer 422 to record the maximum value of pulse pressure (or other selected parameter); greater degrees of compliance in the mechanism tend to reduce the magnitude of the peak pressure observed, thereby potentially making the identification of the pulse pressure peak more difficult.

It will be recognized, however, that alternate configurations having at least some degree of compliance may be utilized in some applications. For example, in one alternate embodiment, a rigid coupling of the applanator assembly to the wrist brace 410 is used; however, a somewhat flexible applanator body 414 with a curved interior surface (not shown) that can adapt to the curvature of the subject's wrist may be utilized. In this fashion, the coupling remains rigid, but the applanator body complies in a limited fashion to the subject's wrist curvature, thereby allowing for a substantially uniform level of contact across a broader portion of the wrist. The degree of compliance of the body 414 is controlled by its flexural strength; i.e., the level of force needed to incrementally deform the body increases as a function of its compliance or "bending", thereby effectively limiting its total compliance, and causing the contact pad 441 mated thereto to preferentially compress after a certain degree of deformation occurs. Other alternatives readily fashioned by those of ordinary skill may be used as well.

Advantageously, any number of different wrist brace configurations may be used consistent with present invention. For example, the brace disclosed in Assignee's co-pending U.S. patent application Ser. No. 09/815,982 previously incorporated herein by reference may be used. Other configurations may also be substituted with equal success, such configurations being readily fashioned by those of ordinary skill in the mechanical arts.

This foregoing flexibility in wrist brace configuration also underscores another benefit of the present invention, specifically that the aforementioned applanation mechanism (and associated technique described in detail below) is somewhat less sensitive to variations in attitude of the applanator and pressure transducer relative to the surface of the subject's skin than prior art techniques and apparatus. This comparative insensitivity relates in part due to the fact that pressure is coupled through the tissue and blood vessel wall over a fairly broad range of arc with respect to the longitudinal axis of the blood vessel, such that angular misalignment (i.e., angles of pressure transducer incidence which depart from a vector normal to the skin's surface at the point of measurement) has less effect. Furthermore, since the first applanation element 402 contacts a broad area of tissue around the blood vessel and compresses/distorts it to some degree, some angular misalignment or rotation of the applanation element contact surface 440 with respect to the skin surface can be tolerated.

The contact pad 441 of the applanation element 402 is formed in the present embodiment of a compressible, pliable foam-like cellular urethane material marketed by Rogers corporation as Poron™, although other materials with similar qualities may be used in conjunction with or in place of the Poron disclosed herein. Poron has, among other properties, a desirable durometer characteristic which is well adapted to the present application. The contact pad 441 is made approximately 0.25 in. (6.35 mm) thick, although other thicknesses may be used. The Assignee hereof has noted during various field trials that the Poron material provides excellent physical properties with respect to the compression of the subject's tissue and blood vessel, thereby very effectively mitigating the aforementioned transfer losses associated with these structures. Additionally, the contact pad 441 of the present embodiment is made replaceable by the user/subject so as to permit maintenance of a hygienic (or even sterile) environment. For example, the pad 441 may be replaced for each use, along with replacement of the pressure transducer assembly, or for each different subject if desired. The use of a low cost polymer advantageously makes the cost of maintaining the device quite low.

Figure 4B:
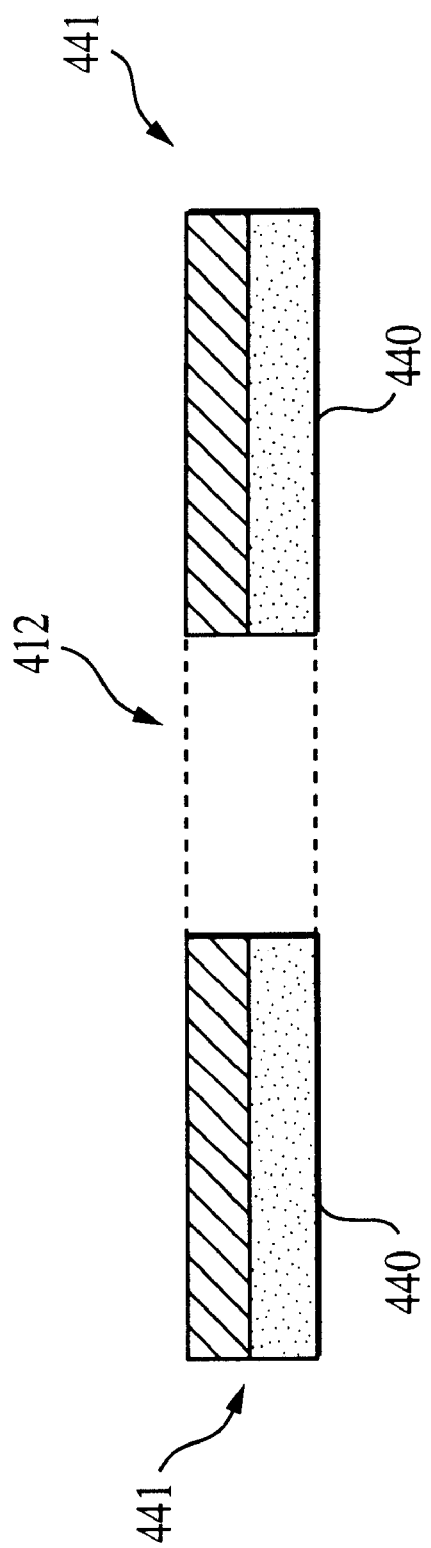
FIG. 4b is a side cross-sectional view of a second embodiment of the contact pad, illustrating the use of multiple layers of material.
Figure 4C:
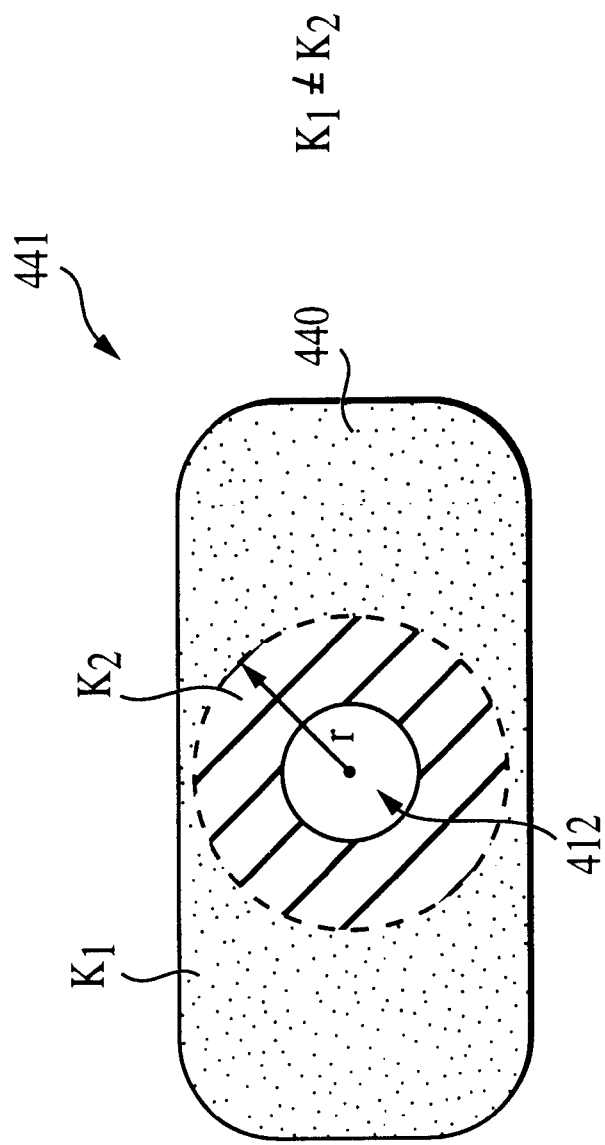
FIG. 4c is a bottom plan view of a third embodiment of the contact pad, illustrating the use of materials which vary as a function of radius from the center applanation element.

It will further be appreciated that while the contact pad 441 described above and showed in FIG. 4*a* is made of both substantially constant thickness and uniform material composition, either of these parameters may be varied for specific applications. For example, the pad 441 can be constructed using a multi-layer or "sandwich" approach, with the physical properties of the various layers being varied so as to provide certain properties for the overall pad assembly. In one embodiment, a two-layer pad (FIG. 4*b*) having different compression constants for each layer is used to provide a progressively varying compression of the pad; e.g., one layer of material will preferentially compress first, followed by the second layer when the incremental compression force of the first layer exceeds that of the second layer. In another embodiment, the material properties are varied in a generally radial direction with respect to the center aperture so as to provide varying rates of compression as a function of radius from the contact point with the tissue overlying the blood vessel (FIG. 4*c*). In yet another embodiment (FIG. 4*d*), the thickness of the pad is varied as a function of spatial position so as to provide varying rates of tissue compression.

Based on the foregoing, it will be appreciated that the configuration of the pad 441 may be "tuned" as needed to accomplish specific rates of tissue compression and/or provide other desired performance attributes. The design and fabrication of such alternate embodiments is well known to those of ordinary skill in the mechanical and materials arts, and accordingly is not described further herein.

Figure 4D:
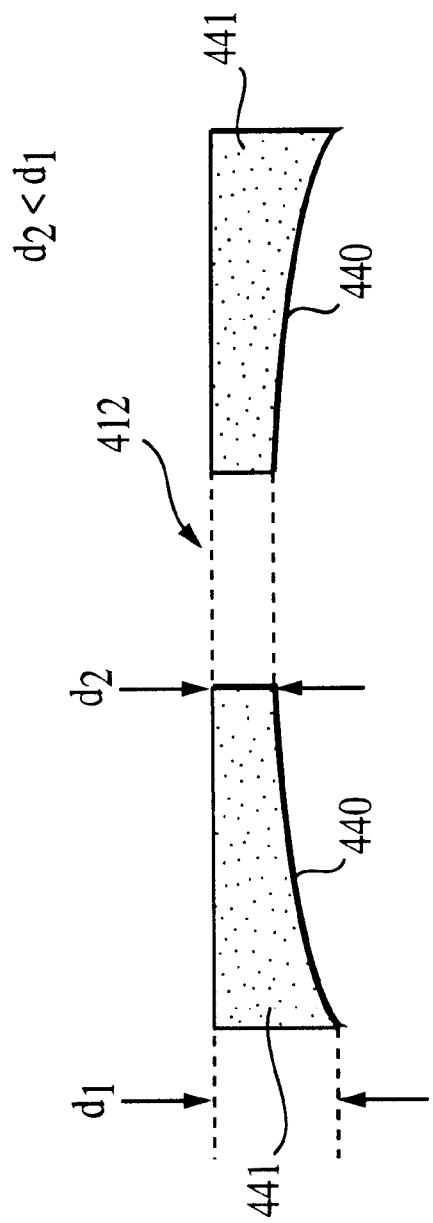
FIG. 4d is a side plan view of a fourth embodiment of the contact pad of the invention, illustrating the use of varying pad material thickness.
Figure 4F:
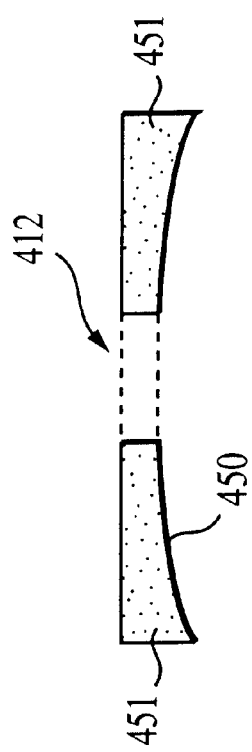
FIGS. 4e–4f are bottom and side plan views, respectively, of a fifth embodiment of the contact pad of the invention.
Figure 4E:
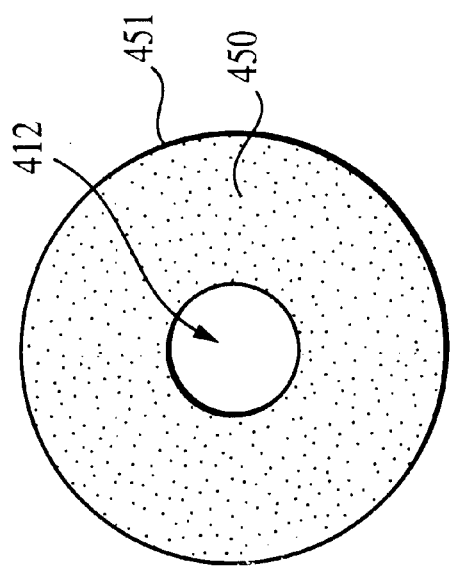
Figure 4H:
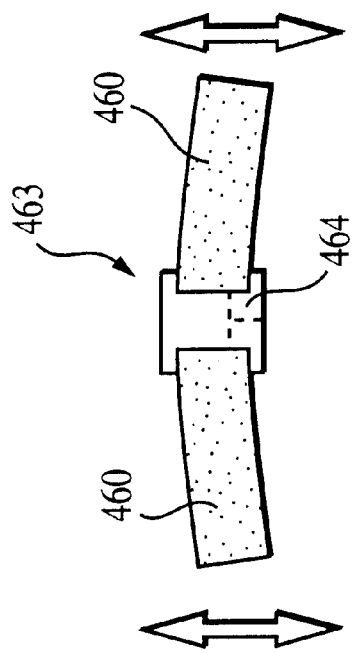
FIGS. 4g–4h are bottom and side plan views, respectively, of a sixth embodiment of the contact pad of the invention.
Figure 4G:
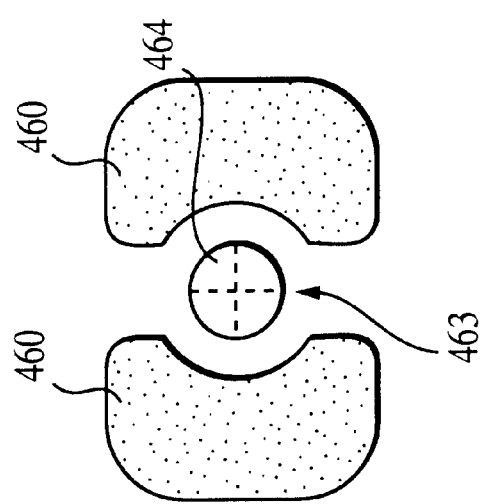

Additionally, while the embodiments of FIGS. 4–4*d* comprise a substantially planar, rectangular pad 441 with a centrally located aperture having a circular cross-section, it will be recognized that other shapes and/or configurations may be used. For example, as shown in the embodiment of FIGS. 4*e*–4*f*, the pad 451 of the applanation element comprises a circular cross-sectional shape with a slight concave arc formed in the contact surface 450 such that the pad conforms to the interior surface of the wrist 455. As yet another alternative (FIGS. 4*g*–4*h*), the applantion element pad may be configured a set of discrete lateral pads 460 disposed on either side of a multi-element array 463 of pressure transducers 464. Myriad other combinations of applanator shapes, sizes, footprints, planarities, and configurations may be used consistent with the present invention, all such combinations falling within the scope of the claims appended hereto.

The motors 406 used in the illustrated embodiment of FIG. 4 to drive the applanation element 402 is a precision "stepper" motor of the type well known in the motor arts. This motor also includes one or more position encoders (not shown) which provide an electrical signal to the host system processor and associated algorithm to very precisely control the position of the applanation element during operation. Accordingly, as described in greater detail below, the variable used in the present embodiment to represent applanation element position is the number of motor steps (positive or negative relative to a "zero" point); this approach advantageously removes the need to measure the absolute position with respect to the subject's tissue or anatomy. Rather, the relative number of steps is measured via the position encoder, and this is effectively correlated to pressure measurement obtained from the pressure transducer(s).

A detailed discussion of the electronic and signal processing apparatus used to support the operation of the applanation mechanism 400 of FIG. 4 is provided with respect to FIG. 7 below.

Methodology

Figure 5:
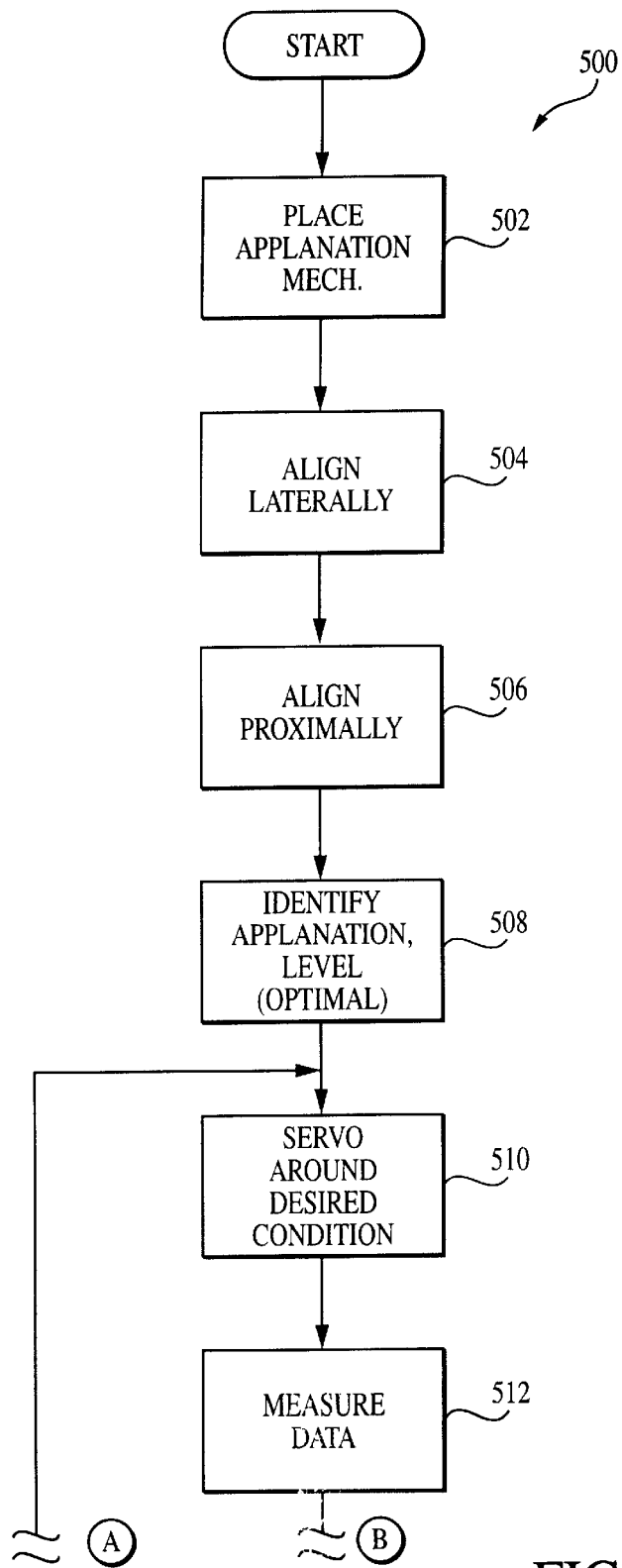
FIG. 5 is a logical flow diagram illustrating one exemplary embodiment of the general method of measuring blood pressure using optimized applanation and scaling according to the invention.
Figure 5:
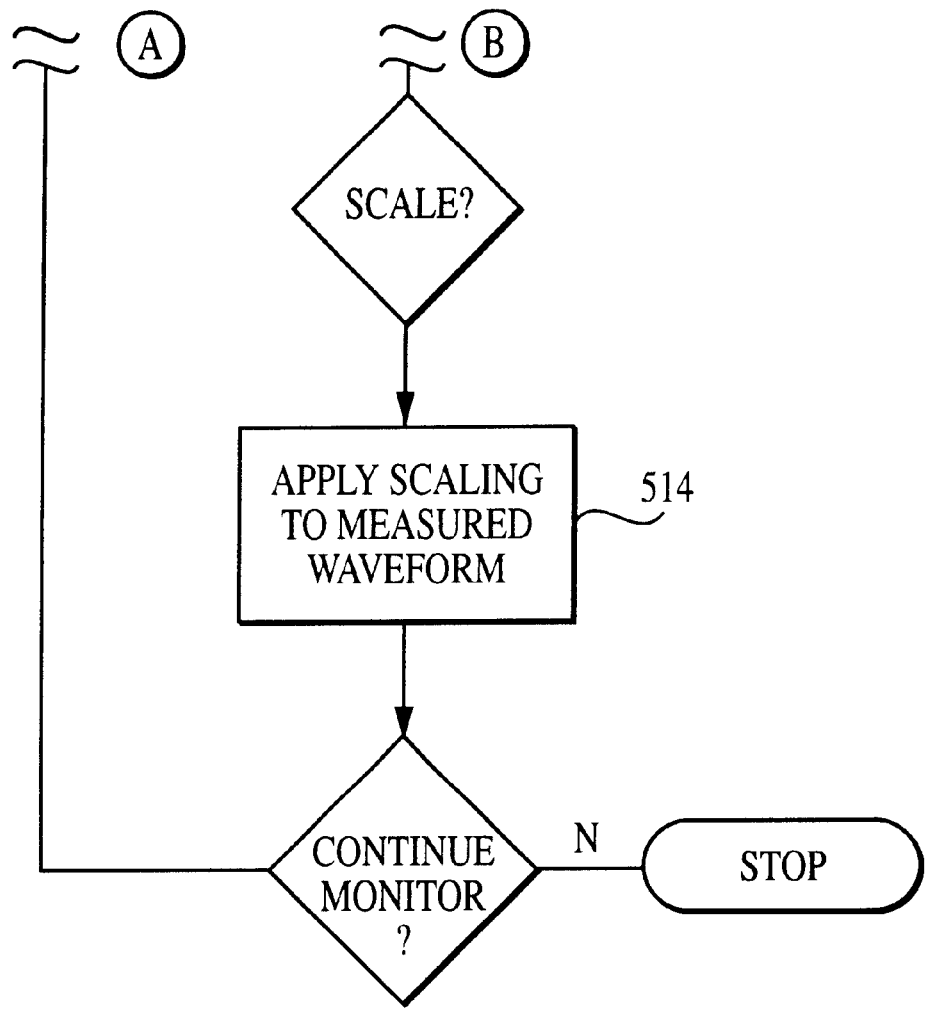

Referring now to FIG. 5, the general methodology of optimally applanating or compressing the blood vessel and local tissue utilizing the previously described apparatus is described in detail.

As previously discussed, one fundamental concept of the present invention (and hence the methodology presented below) is to control the applanation element 402 such that the transfer loss associated with the tissue and structures surrounding the blood vessel is mitigated during measurement. In the case of the human radial artery, the transfer loss is effectively mitigated at that level of applanation where the tonometrically measured pulse pressure is maximized. Too little compression, and the coupling between the blood vessel wall and tissue surface (and hence transducer active surface) is incomplete, yielding tonometric pressure values which are significantly in error. Too much compression, and the vessel wall collapses, thereby distorting the cross-sectional shape of the vessel significantly, and again producing high levels of error. The optimal condition is to couple the vessel wall through the interposed tissue as completely as possible without otherwise affecting the hemodynamics of the vessel itself.

As shown in FIG. 5, the first step 502 of the method 500 comprises placing the applanation mechanism 400 in the position with respect to the subject's blood vessel. Such placement may be accomplished manually, i.e., by the caregiver or subject visually aligning the transducer and device over the interior portion of the wrist, by the pressure/electronic/acoustic methods of positioning previously referenced, or by yet other means. Ideally, the applanation element 402 and its contact pad will be comfortably situated transversely over the interior of the wrist, with the transducer element 422 directly overlying the radial artery with little or no inclination with respect thereto. The element 402 and transducer 422 may be laterally aligned (step 504) and proximally aligned (step 506) if required. In one exemplary embodiment, the tonometrically measured pressure signal obtained from the transducer 422 may be used as a basis for such lateral/proximal positioning, in a manner similar to that used for determining optimal applanation level (described in detail below).

Figure 5A:
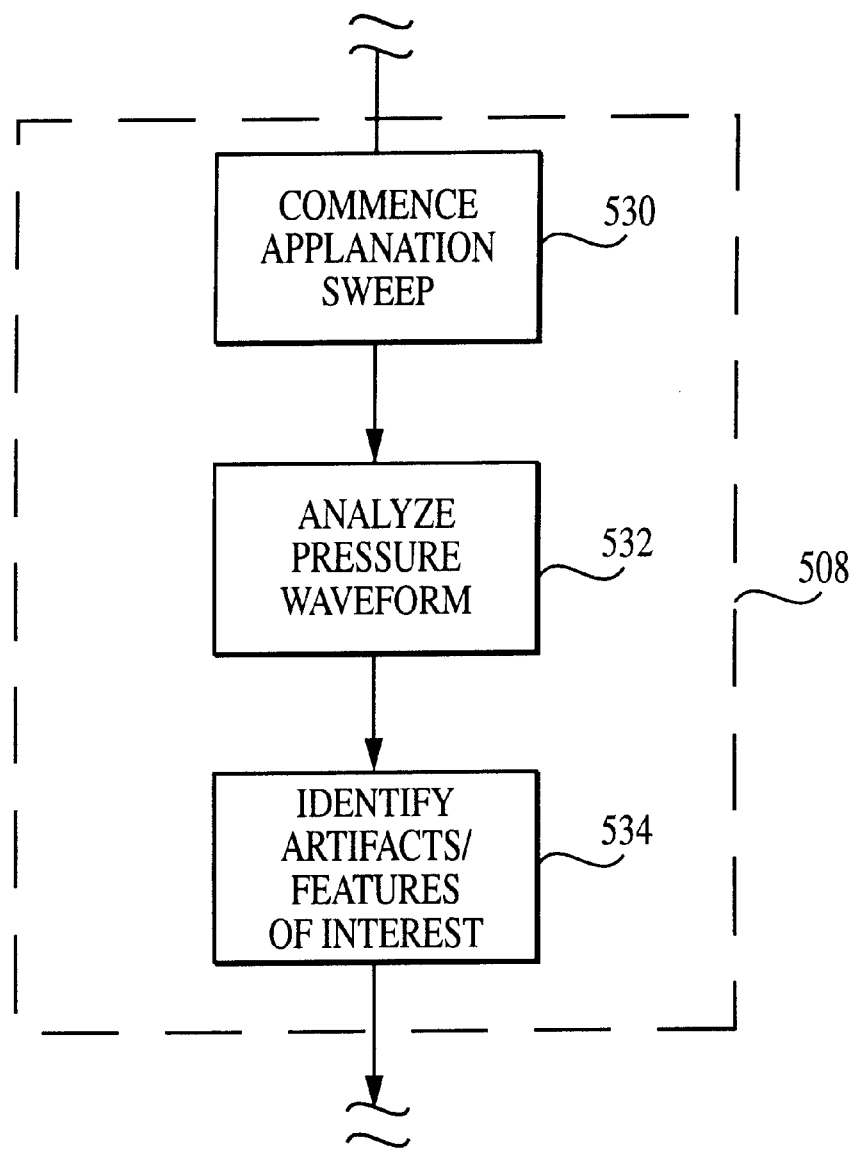
FIG. 5a is a logical flow diagram illustrating one method of scaling an unscaled tonometric waveform using body mass index and pulse pressure.

Once the applanation element 402 is suitably located and oriented, the element 402 is operated per step 508 so as to applanate the tissue surrounding (and at least partly overlying) the blood vessel to a desired level so as to identify an optimal position where the effects of transfer loss and other errors associated with the tonometric measurement are mitigated. Specifically, as shown in the embodiment of FIG. 5a, an applanation sweep is commenced (step 530) using the motor 406 driving the element 402, thereby progressively increasing the pressure applied to the tissue by the contact pad 441. During this sweep, the pressure waveform obtained from the transducer 422 is analyzed on an interval (e.g., per-beat) basis per step 532 so as to determine the value of pulse pressure for that interval. Such calculations are generally accomplished within such a short duration (owing largely to the signal processing apparatus described below with respect to FIG. 7) with respect to the rate of change of applanation such that the necessary calculations can be made "on the fly" during the applanation sweep. Certain artifacts or conditions existing within the waveform are identified (step 534), thereby indicating that the desired level of applanation has been reached. For example, in the embodiment of FIG. 5a, the pulse pressures are calculated for each contiguous heart beat interval. "Peak-to-trough" amplitude values of the waveform for each interval are determined as part of this calculation in the present embodiment, although other quantities and/or portions of the waveform may be utilized. Where the calculated pulse pressure decreases below a certain percentage (e.g., 50%) of a prior beat for a designated number of beats (e.g., two), a pulse pressure "maximum" is declared, and level of applanation is reduced back to that corresponding to the prior beat interval where pulse pressure was maximized (step 510 of FIG. 5).

The coarse positioning of the applanation element 402 back to the position of maximum pulse pressure is accomplished in one embodiment using the motor position recorded during the applanation sweep (e.g., at a given number of motor steps which corresponds to the level of arterial applanation or compression where maximum pulse pressure was detected). Once the coarse position is obtained and the applanator returned to this position, the system then is permitted to "settle" for a period of time, and an iterative "search" approach is utilized to vary the position of the applanation motor and element in each direction; i.e., more applanation and less applanation, while monitoring mean pressure as determined from the pressure transducer 422 (and supporting circuitry). A "maximum" detection routine is utilized as part of this iterative movement to verify that in fact the maximum point has been achieved and, if required, move the applanation element to that point from the current position. It is noted that while the motor position or similar indicia corresponding to the maximum pulse pressure is generally a good "coarse" positioning determinant, other factors (physiologic and otherwise) may cause the level of optimal applanation to vary somewhat, thereby necessitating the maximum detection routine referenced above for best results. However, depending on the level of accuracy desired, the "coarse" repositioning criteria may be used alone if desired.

It will be recognized that a variety of different applantion sweep profiles may be employed as part of the foregoing steps. Specifically, the simplest profile is probably the straight linear rate sweep, wherein the applanation element drive motor 406 is controlled by the system controller (described below) to move the applanation element at an effectively constant rate (e.g., 5000 motor steps/min). This produces a non-linear application of force or bias to the tissue being compressed, since more force will be required to compress the tissue as it is nearing full compression as opposed to the onset of applanation. As another alternative, the applantion sweep may be step-wise linear; i.e., a contiguous set of mini-sweeps of constant rate punctuated by finite pause periods of no motion. This approach may be useful where significant signal processing or other data processing/acquisition is required during the applanation sweep.

Figure 5B:
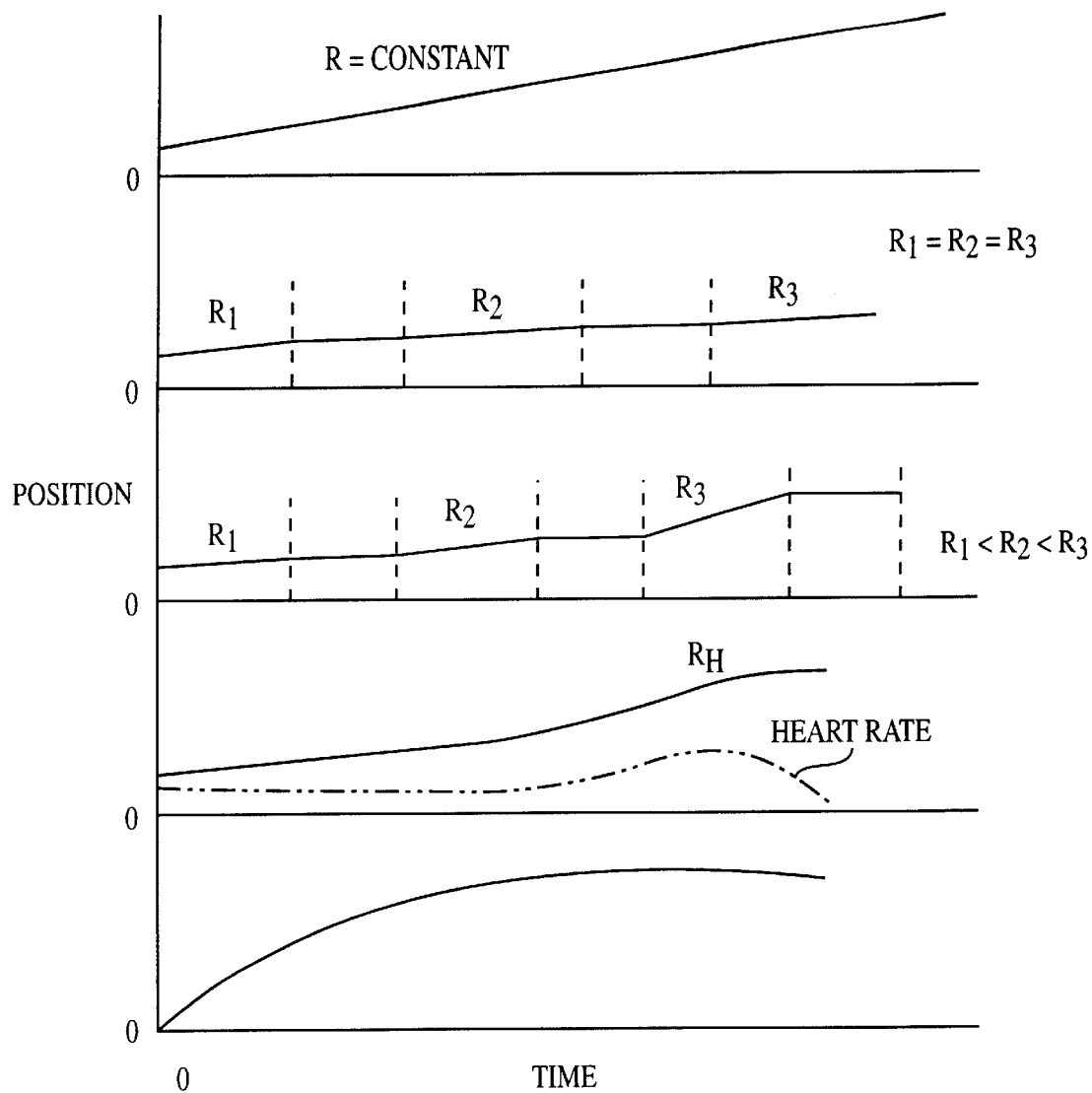
FIG. 5b is a graph illustrating a plurality of alternative applanation sweep profiles useful with the present invention.

As yet another alternative, the rate of applanation may be made deterministic. For example, in one alternative embodiment, the rate is coupled to the patient's heart rate, which is determined either directly by the hemodynamic measurement system (i.e., extracted from the pressure waveform measured by the pressure transducer 422 through signal processing), or by another apparatus (such as an electrocardiographic device adapted to analyze the QRS complexes of the heart). Specifically, in one embodiment using the indigenous determination via the measured pressure waveform, the extracted heart rate is entered into a linear equation of the form y=mx+b, such that for a high subject heart rate, the rate of applantion is set proportionately high, and vice versa. Clearly, however, non-linear functions may be substituted if desired. FIG. 5b graphically illustrates a number of the foregoing alternatives.

Additionally, other deterministic, quantities may be used as the basis for the applanation rate determination. For example, the values of systolic and/or diastolic blood pressure (or derivations thereof) may be used as inputs to an applanation rate equation. Myriad other variants may also be used, either alone or in combination, so as to best select the proper applanation rate under varying subject physiologic conditions.

Next, per step 512 of the method 500 of FIG. 5, the desired pressure value(s) are measured and stored in the system's storage device, discussed below, while the applanation is set at (or servoes around) that point where pulse pressure is maximized. For example, in one embodiment, the systolic and diastolic waveforms are extracted from the pressure transducer output signal. It is noted that in the case of the exemplary human radial artery, the point of applanation at which maximum pulse pressure occurs correlates strongly to mean arterial blood pressure, with the degree of correlation being affected to some degree by the shape, size, footprint, compliance, and other properties of the contact pad 441 previously described herein with respect to FIG. 4.

Next, in step 514, the measured values of the hemodynamic values (e.g., pressure) are optionally scaled or corrected for transfer loss as appropriate. It will be recognized that not every measured value will need to be scaled, and in some cases no scaling will be required. This result stems from the fact that (i) different individuals have different physiologic features and construction, thereby allowing the transfer loss associated with one individual to be markedly different from another; and (ii) the magnitude of the transfer loss (and hence the error in the tonometric measurement as compared to the actual intra-vascular pressure) may be small so as to be inconsequential. As will be described in subsequent discussion herein, there is a strong correlation between the magnitude of the transfer loss for a given individual and their body mass index (BMI), thereby allowing the present invention to, inter alia, "intelligently" scale the raw measured hemodynamic parameters.

Figure 5C:
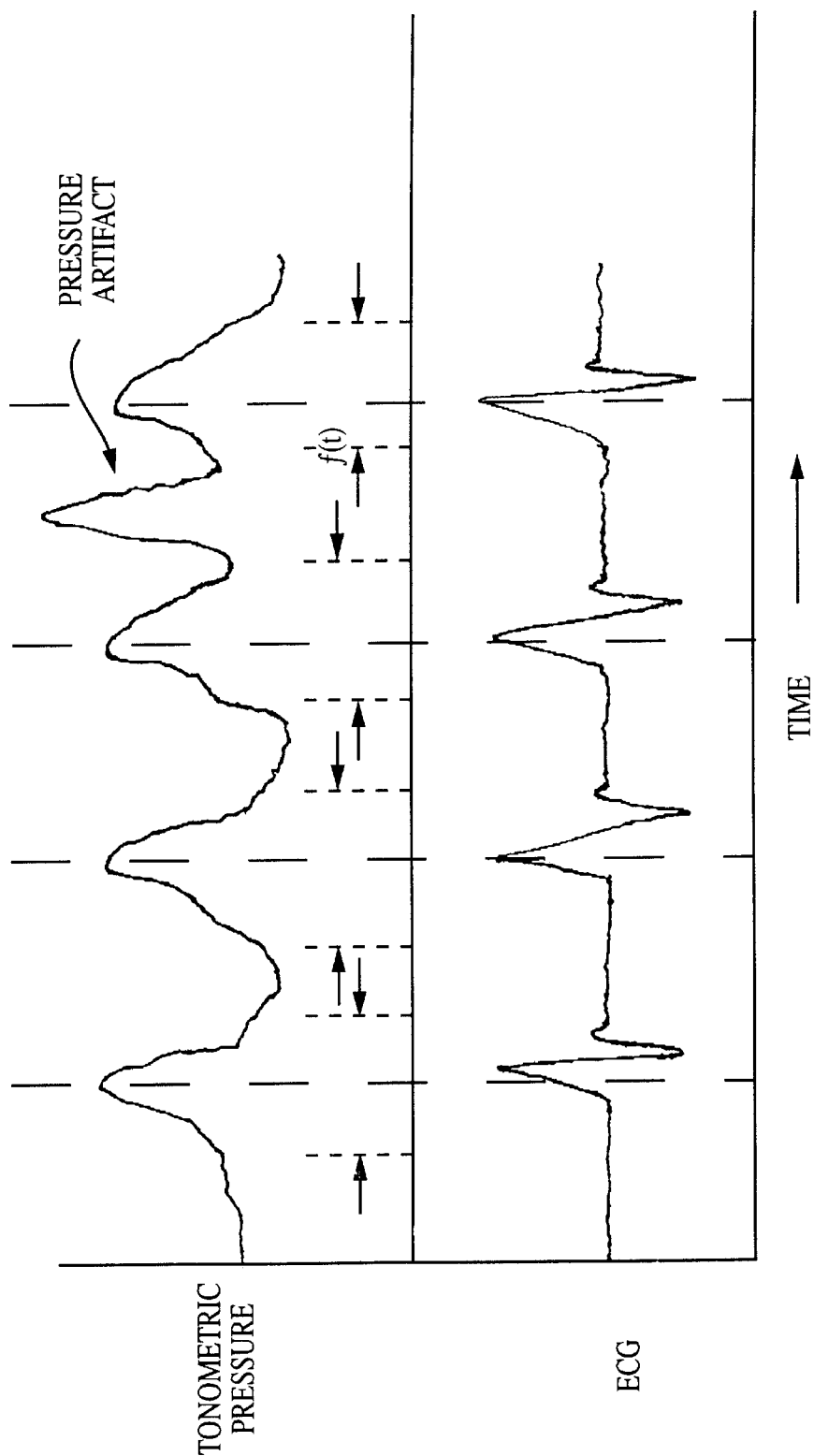
FIG. 5c is a graph showing one exemplary method of identifying and eliminating noise artifact from a tonometric pressure waveform using an external signal.

It is noted that the present invention may also utilize the heart rate signal provided by the aforementioned ECG or other external device as a synchronization signal to aid in identifying artifacts or other features in the tonometrically obtained pressure waveform. Specifically, since the ECG (or other) non-indigenous measurement technique used may not be subject to non-physiologic noise (e.g., movement by the patient, vibration of the treatment facility, low-frequency AC noise, etc.), artifacts present in the pressure waveform can be mapped against the external signal for purposes of correlating and eliminating such artifacts. For example, as is well known, the aforementioned ECG technique uses electrical signals relating to the QRS complex of the subject's heart for measuring heart rate; the ECG waveform will therefore register QRS complexes at the interval they are generated by the subject's heart, largely irrespective of motion artifact or other noise. Hence, wherein the tonometric pressure waveform will display motion artifact (such as the gurney on which the subject is lying being inadvertently kicked by someone administering treatment, or the ambulance in which the subject is riding traversing a rough patch of road) to some degree, such artifacts will generally be absent from the ECG signal. The present invention optionally maps the two signals coincident in the temporal dimension using the digital processor described below with respect to FIG. 7, and examines the signals at a predetermined rate and interval (e.g., a moving 100 ms window every 100 ms), or upon the occurrence of a predetermined event (e.g., ECG QRS amplitude exceeding a given threshold) to determine whether an observed pressure transient should be included in the data collected for that period, or discarded as a spurious noise transient or motion artifact. In one exemplary embodiment (FIG. 5c), the ECG waveform is monitored for the detection of each heart beat; a windowing function f(t) is applied to the tonometrically obtained waveform data to effectively block out pressure transients occurring outside the specified temporal window, which is centered on the ECG-detected "beat". Hence, only those artifacts which are coincident with heart beats as detected by the ECG will be included in the subsequent signal processing of the tonometric waveform. Assuming a random distribution of noise/artifact, the great majority of such noise/artifact will be eliminated from the pressure waveform using such a technique.

It will be appreciated, however, that other functions and approaches to correlating the external signal (ECG or otherwise) and the tonometric waveform may be used. For example, rather than a windowing approach which has two discrete states (i.e., discard or not discard), more sophisticated signal processing and filtration algorithms adapted to selectively identify noise/artifact and remove it from the waveform "on the fly" may be employed. Such algorithms are well known to those of ordinary skill in the signal processing arts, and accordingly are not described further herein.

BMI/Pulse Pressure (PP) Scaling

Referring now to FIGS. 5d–5h, one exemplary embodiment of the methodology for scaling or correcting raw or unscaled hemodynamic data obtained using the methodology of FIG. 5 described above. It will be recognized that while the embodiment of FIGS. 5d–5h is described in terms of an algorithm such as would be utilized in conjunction with a digital computer system having a microprocessor or signal processor, the method of the present invention may be partially or even entirely practiced independent of such an algorithm or computer system. For example, portions of the algorithm may be accomplished via hardware (such as gate logic embodied in an ASIC or FPGA), or even manually via direct or indirect control of the operator. Accordingly, the exemplar of FIGS. 5d–5h is merely illustrative of the broader concepts.

Figure 5D:
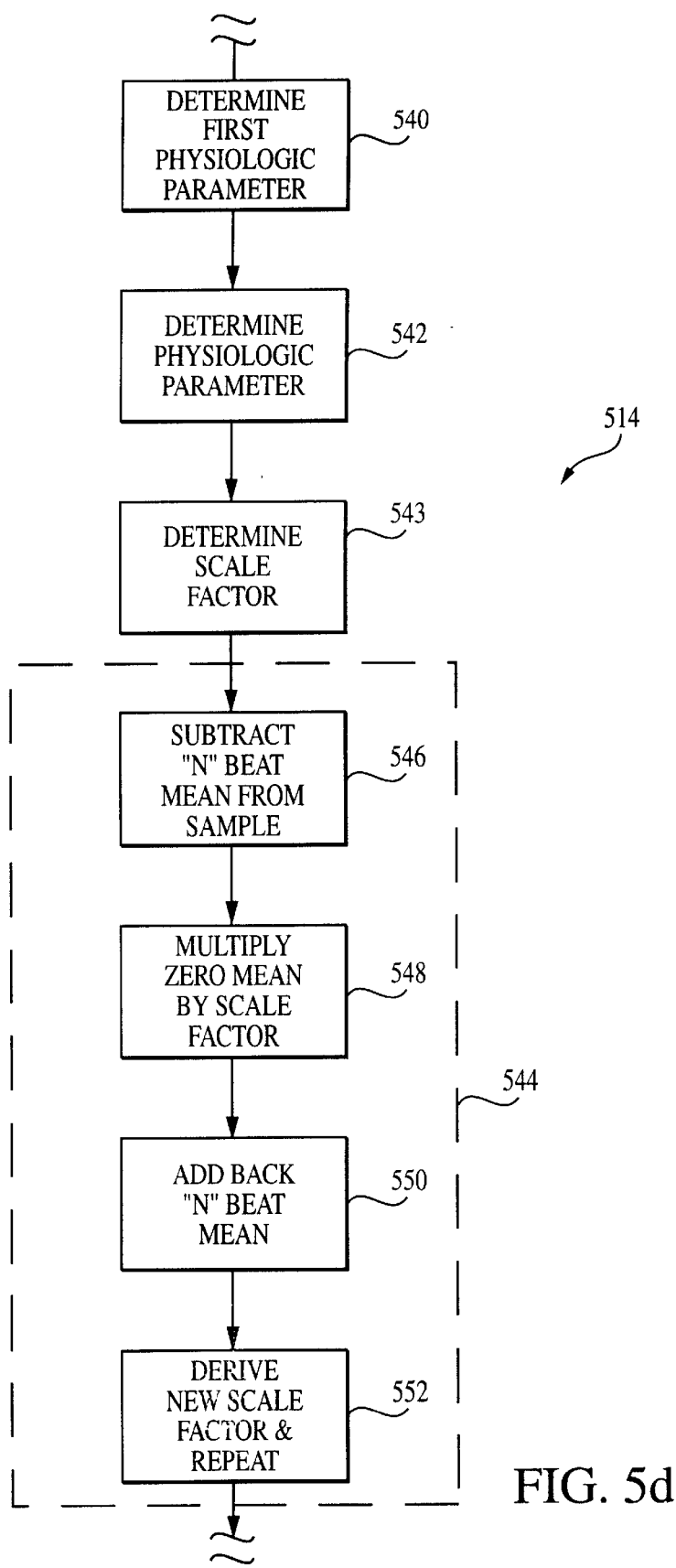
FIG. 5d is a logical flow diagram illustrating one exemplary embodiment of the method of scaling hemodynamic measurements (using BMI and PP) according to the invention.

As illustrated in FIG. 5d, the method of scaling 514 generally comprises first determining a first physiologic parameter of the living subject under evaluation (step 540). For the sake of illustration, the method 514 is described in terms of the scaling of a tonometrically obtained blood pressure measurement obtained from the radial artery of a human being, although it will be appreciated that the method may be employed at other monitoring locations on the same or different species. The first parameter obtained in this exemplary embodiment comprises a body mass index (BMI) of the type well known in the medical arts. Specifically, the BMI comprises:

$$BMI = W/H^2 \qquad \text{(Eqn. 1)}$$

where:
BMI=Body mass index (Kg/m)
W=Subject weight (kgf)
H=Subject height (m)

Typical BMI values for the human species range from about 15 Kg/m$^2$ up to roughly 50 Kg/m$^2$, although values outside this range may occur. The values of subject weight (W) and height (H) are readily obtained using conventional measurement techniques not described further herein.

Next, a second physiologic parameter of the same subject is determined in step 542. In the method embodiment of FIGS. 5d–5h, the pulse pressure (i.e., the systolic pressure minus the diastolic pressure) is used in conjunction with the body mass index (BMI) of the subject to generate a corrected pulse pressure.

Figure 5E:
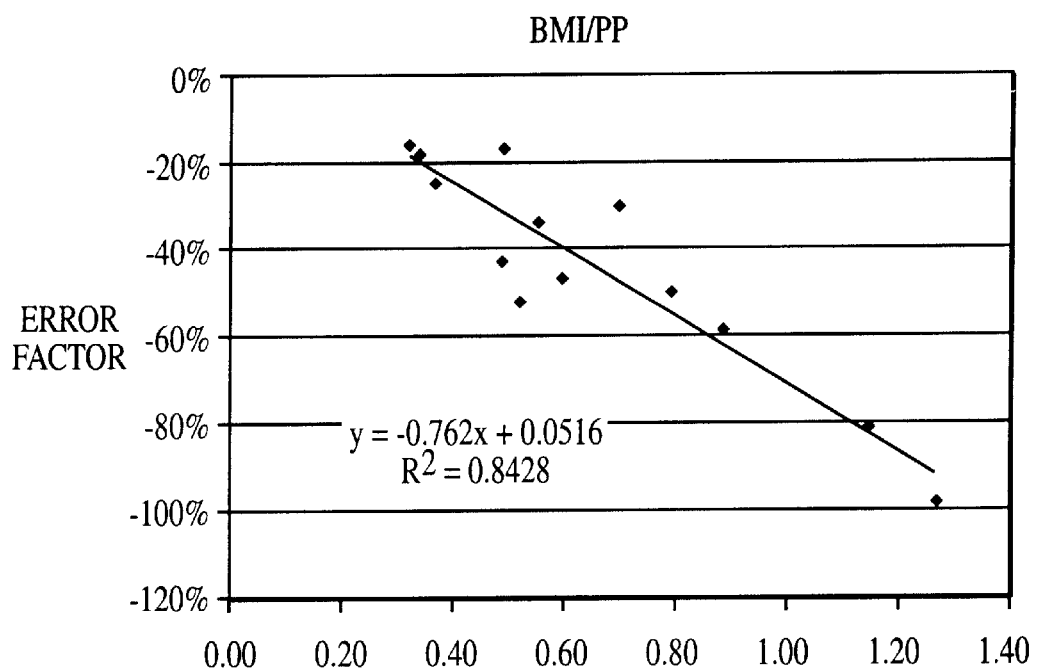
FIG. 5e is a graph showing the relationship between BMI/PP and error factor for radial artery data derived from a sample of human beings.

FIG. 5e illustrates the relationship (based on empirical data derived by the Assignee hereof, discussed in greater detail below) between the ratio of BMI to tonometrically measured pulse pressure (PP) and the error factor (percentage error between tonometrically derived pressure reading, and the actual intravascular pressure as determined by A-line invasive catheter). As shown in FIG. 5e, the relationship between error and BMI/PP is well grouped and substantially linear for the data presented, the latter spanning a broad range of BMI/PP values.

FIG. 5e is significant from the standpoint that it provides a description of the behavior of error as a function of certain selected physiologic parameters (e.g., BMI and PP). This description allows the present invention to apply the appropriate level of scaling to the tonometric pressure measurements to correct for transfer loss and related errors present in these measurements. As shown in FIG. 5e, the losses (as reflected by the error factor) at low BMI/PP values are low, and increase (linearly) as BMI/PP increases. In practical terms, persons with high BMI for the same PP value will require more transfer loss correction, which intuitively follows from the observation that such people commonly have a greater mass of tissue (skin, fat, muscle, tendon, etc.) interposed between the radial artery and surface of the skin on the interior of the wrist. Conversely, a very tall, thin person with average PP value will require little correction for transfer loss, which is also intuitively compelling.

Figure 5F:
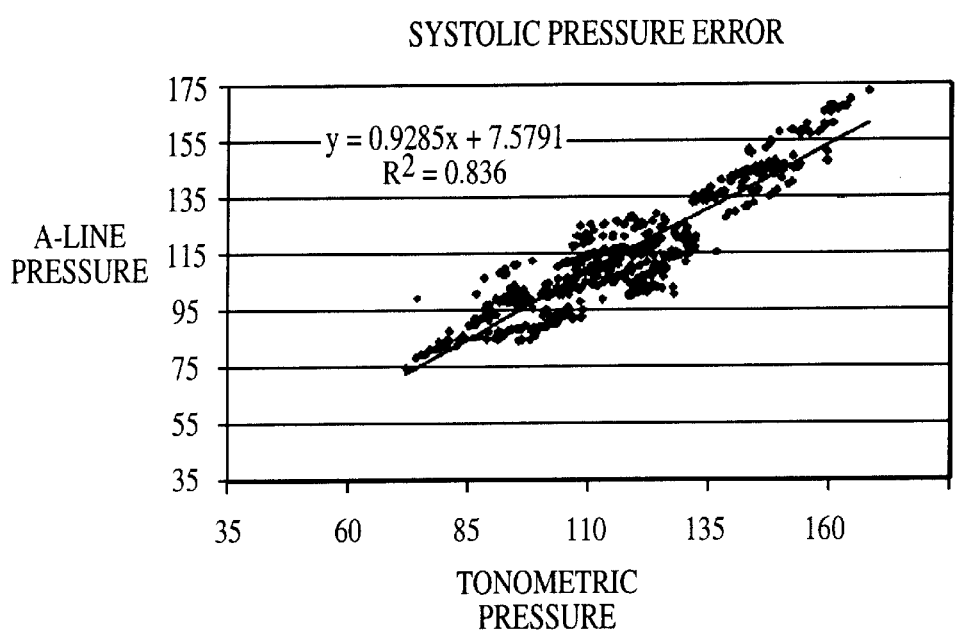
FIG. 5f is a graph showing the relationship between actual and uncorrected tonometric systolic pressure for the sample of FIG. 5e.
Figure 5G:
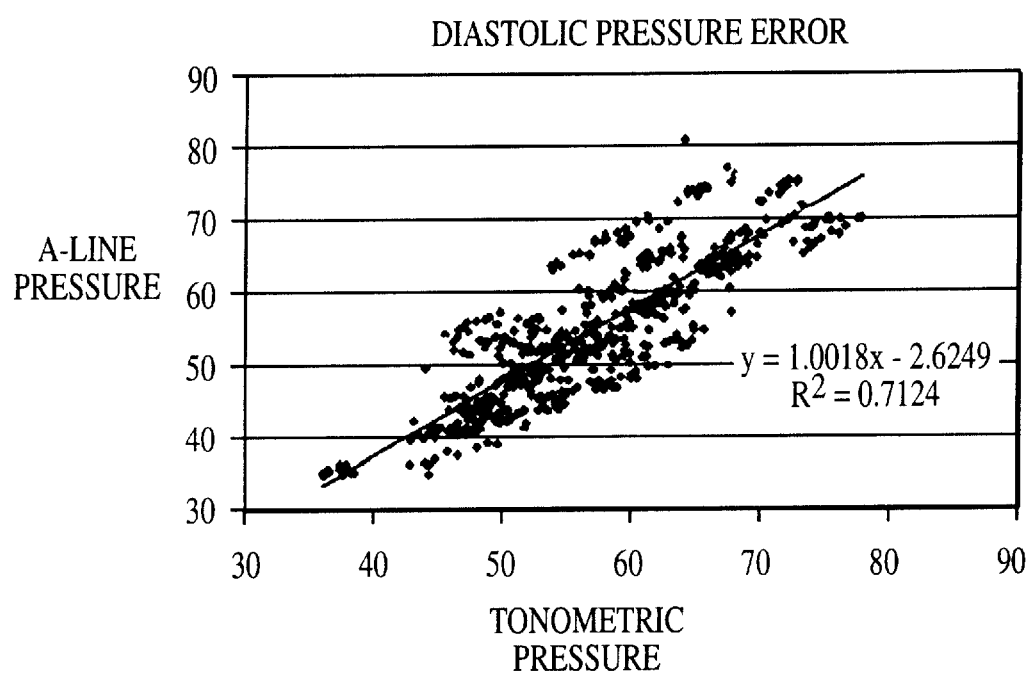
FIG. 5g is a graph showing the relationship between actual and uncorrected tonometric diastolic pressure for the sample of FIG. 5f.

FIGS. 5f and 5g illustrate the relationship between actual intravascular pressure (as measured, for example by an A-line) and tonometrically measured pressure for systolic and diastolic pressures, respectively, for the empirical data previously referenced. As shown in each of these figures, the data is tightly grouped along a functional line (here, modeled as linear). Stated differently, there are predictable functional relationships between the tonometrically measured systolic and diastolic pressures and their corresponding actual intravascular values.

In the present embodiment, a linear relationship is also used to model the percentage error between the tonometric and actual intravascular pressures, as follows:

$$\% \text{ Error} = \frac{PP_T - PP_A}{PP_T} = M \cdot \frac{BMI}{PP_T} + b \quad \text{(Eqn. 2)}$$

Where:
$PP_T$=pulse pressure (tonometric)
$PP_A$=pulse pressure (actual)
M=slope
b=intercept
Manipulating this equation, the following is obtained:

$$PP_T - PP_A = M \cdot BMI + b \cdot PP_T \quad \text{(Eqn. 3)}$$

$$PP_T - b \cdot PP_T - M \cdot BMI = PP_A \quad \text{(Eqn. 4)}$$

and $$PP_T(1-b) - M \cdot BMI = PP_A \quad \text{(Eqn. 5)}$$

Eqn. 5 is the generalized relationship relating the actual intravascular pressure ($PP_A$) and the tonometric pressure ($PP_T$) based on BMI. Note that PPA (also referred to as the corrected pulse pressure, $PP_c$) is based on the current interval (e.g., beat), while $PP_T$ is based on an average pulse pressure over the prior "n" pulses. Here, "n" can be any number (e.g., 10), or made deterministic such as being based on another quantity measured from the subject or otherwise derived in the calculation process if desired. Hence, in effect, the ratio $PP_C/PP_T$ is the scale factor which is applied to subsequent samples of the tonometrically obtain pressure waveform. An "n" interval moving window is established, wherein the same scale factor is applied over each interval (beat).

Despite the use of a linear relationship in Eqn. 5 above (and the functions of FIGS. 5f and 5g), it will be appreciated that the relationship between the BMI/PP and error factor (or for that matter any other physiologic parameters or function thereof used for scaling) need not be linear or assume any prescribed form. For example, data collected on the population as a whole or subsets thereof (e.g., those within a specific BMI range) may be decidedly non-linear. Furthermore, other parametric relationships such as the BMI/WC approach described below may yield a non-linear function, which can be used as the basis for scaling. Alternatively, the function may be piecewise-continuous or even discontinuous. Myriad functional relationships therefore may be successfully substituted and used consistent with the general premise of the present invention.

Returning to FIG. 5d, the corrected (scaled) pressure waveform is next derived per step 544. In the present embodiment, this is determined by (i) subtracting the average "n" pulse tonometrically measured mean pressure from each subsequent tonometric sample value of pressure (a "zero mean" sample result) per step 546; (ii) multiplying each "zero mean" sample value derived in (i) by the derived scale factor (step 548), and adding back the "n" beat average mean pressure value (step 550); and (iii) repeating the process every "n" beats, using a newly derived scale factor for every "n" beats (step 552). The resultant waveform is a scaled waveform which is effectively corrected for transfer loss.

Note that the foregoing "zero mean" approach is used so as to zero or center the waveform around a known reference level (zero). In this fashion, systolic pressure measurements advantageously will always be above the zero mean, and diastolic pressure measurements always below. However, a non-zero mean (i.e., offset) or other reference point may be chosen if desired, such as any value between zero and the measured pressure mean. The zero-mean approach is merely an expedient convention to simplify analysis and make the results more intuitive to the user/operator. It will be appreciated that such value(s) may be chosen to facilitate computational efficiency, especially in more "thin" hardware environments where computational capacity of the host platform is minimal or at a premium. For example, a low cost (or even disposable) apparatus embodying the present invention may have a digital processor with very limited MIPS and/or memory; the mean or offset point can therefore be chosen so as to best optimize this limited capability.

Figure 5H:
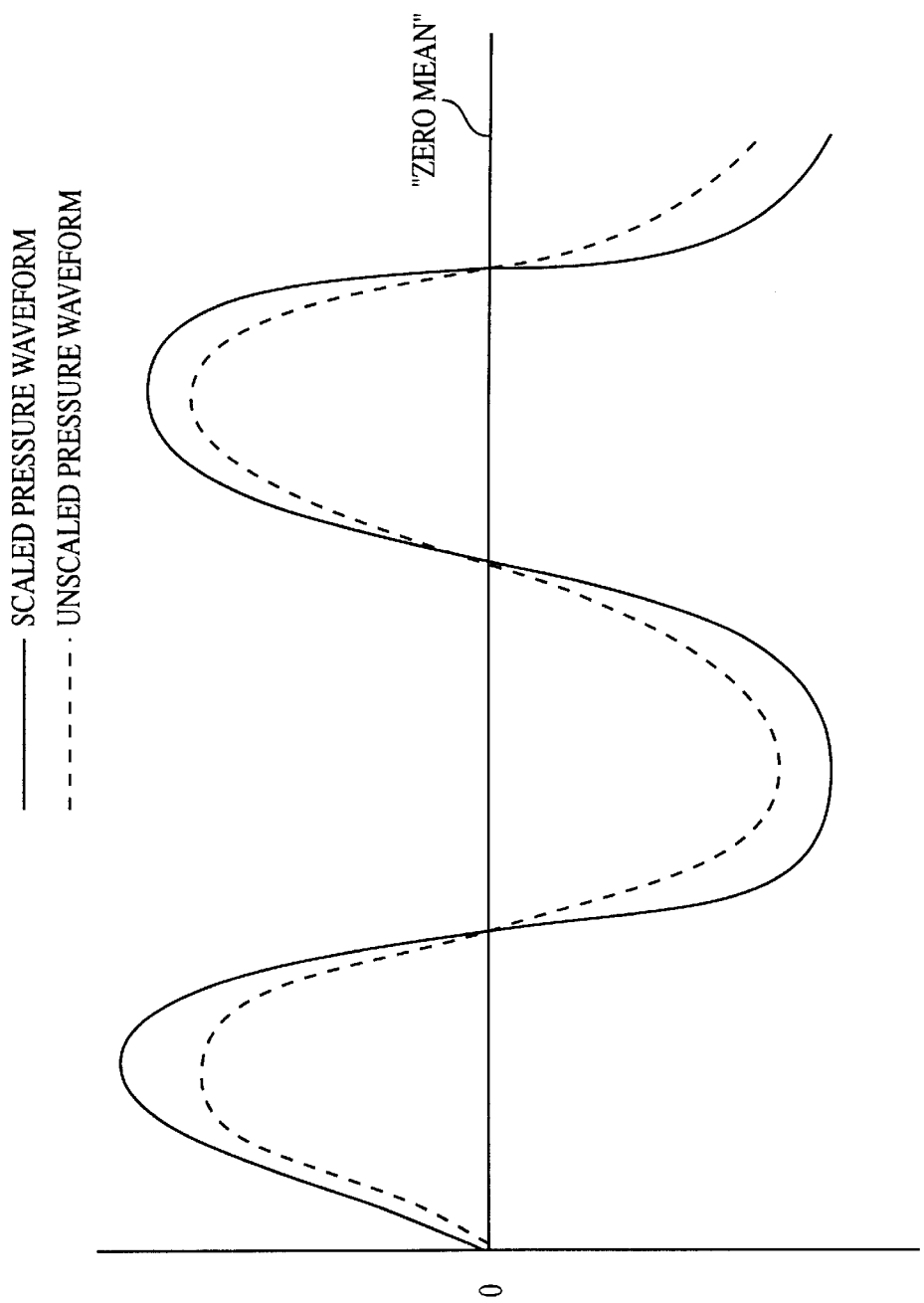
FIG. 5h is a graph showing an exemplary "zero mean" tonometric pressure waveform before and after being corrected (scaled).

It is also noted that the magnitude of error associated with the tonometric measurements described herein is always negative (FIG. 5d is entirely on the "negative" side of the error factor scale). This correlates to the tonometric pressure always being less than the actual intravascular pressure in magnitude due to transfer loss. When this fact is coupled with the "zero mean" technique described above, it results in tonometric systolic and diastolic pressure values which always must be increased in magnitude during scaling ("stretched up" for systolic, and "stretched down", as shown in FIG. 5h). As described in greater detail below with respect to FIG. 7, the apparatus 700 of the present invention calculates a "stretch" value based on BMI and PP according to the previously discussed methodology which performs this stretching of the tonometric waveform so as to comply with the actual intravascular waveform.

The use of pulse pressure (PP) as a physiologic parameter in the present embodiment provides the further advantage of being derived from other variables measured by the pressure transducer. That is, PP is derived by a mathematical manipulation of the systolic and diastolic pressure values at any given time (or over a predetermined interval); accordingly, in the exemplary embodiment of the invention wherein the scaling factor determination is performed algorithmically using pressure values obtained intrinsically by the system during pressure measurement, there is no need for the caregiver or subject to measure such parameter. This advantageously simplifies the scaling process.

As previously noted, the data presented above was obtained by the Assignee while conducting clinical trials in validation of the methodology of the present invention. Specifically, the Applicant selected a number (>20) of individuals at random, and obtained multiple tonometric waveforms for each. This generated in excess of 500 data files relating to these individuals. Each data file was broken into a plurality of "epochs" (e.g., 10-beat increments), with the pressure value being averaged over each epoch. The aforementioned BMI-based scaling was applied to each averaged epoch, with all scaled epochs ultimately being collectively analyzed to generate "global" or non-individual specific data. The radial artery of one arm of each individual was arbitrarily chosen as the basis for the measurements, while the other arm of the same individual(s) was utilized to provide substantially concurrent A-line invasive catheter measurements of blood pressure. Results of this "proof of principles" testing yielded very low errors in both systolic and diastolic measurements of roughly −1.2 mmHg (std. deviation=8.6) and −2.6 mmHg (std. deviation 5.4), respectively, after scaling as compared to the corresponding A-line values, thereby validating the methodology experimentally. Note that based on the required +/−5 mmHg (std. deviation=8 mmHg) performance level of the well known AAMI SP10 standard relating to auscultation/oscillometric blood pressure measurement techniques, the clinical performance of the present invention is excellent.

BMI/WC Scaling

Referring now to FIG. 5$i$, a second exemplary embodiment of the method of scaling (step 514 of FIG. 5$d$) is described. In this second embodiment, the second physiologic parameter comprises the circumference of the subject's wrist (WC) at the point of measurement. This is functionally related to the BMI previously described to produce a scaling index, as described in greater detail below.

In the first step 562 of the method of scaling 560 of FIG. 5$i$, the BMI value is obtained for the subject as previously described herein with reference to FIG. 5$d$. Next, in step 564, the BMI value determined in step 562 is related to the second parameter (e.g., wrist circumference of the same subject) to obtain a scaling index $I_s$ as defined by Eqn. 6:

$$I_s = BMI/WC \qquad (\text{Eqn. 6})$$

where:

$I_s$=Scaling factor (considered dimensionless)

BMI=Body mass index (Kg/m$^2$)

WC=Wrist circumference (cm)

"Typical" values for $I_s$ range from approximately 2 to 10, although values outside this range may be observed. Note, however, that the term "typical" here refers to values observed over a broad cross-section of the general population, and variations in body type, bone size, weight, body fat content, and the like may cause significant variations in $I_s$ between two individuals.

From the scaling index value $I_s$ determined for each individual, a scale factor $K_s$ is next determined (step 566). Table 1 below illustrates one exemplary approach used to derive the scaling factor $K_s$ from the scaling index $I_s$. This table is derived from empirical data obtained by the Assignee during clinical trials of a statistically significant number of individuals, as compared to auscultation/oscillometry ("cuff") measurements obtained from the same individuals.

TABLE 1

| Scale Index ($I_S$) | Scale Factor ($K_S$) | Remarks |
|---|---|---|
| >4.0 | 1.2 (20%) | Significant fatty tissue present at radial artery |
| 3.3–4.0 | 1.09 (9%) | Some fatty tissue present at radial artery |
| <3.3 | 1.0 (no scaling) | Little fatty tissue present at radial artery |

The embodiment of Table 1 has the advantage of simplifying the $K_s$ determination process, since the $K_s$ value to be applied to the measured blood pressure of the subject is chosen from a limited number of discrete intervals (i.e., $I_s$ value ranges). For example, consider the subject having an $I_s$ value of 2.8. Using Table 1, it can be seen that no scaling of the raw blood pressure measurement is required. This relates primarily to the subject having a comparatively large wrist circumference in relation to their BMI, often indicating the absence of significant amounts of fatty tissue at the measurement site (i.e., radial artery). Less fatty tissue provides more complete "coupling" (less transfer loss) between the pressure transducer and the blood vessel wall, thereby requiring less corrective scaling.

In contrast, consider the individual with an $I_s$ value of 6.0. For this individual, Table 1 indicates that a scale factor $K_s$ of 1.2 should be applied (effectively correcting the observed pressure value upward by 20 percent). Such scaling is needed since the transfer loss for this individual is substantially greater, as reflected in the greater ratio of their body mass index (BMI) to their wrist circumference. Hence, the BMI (numerator) tends to drive or be directly related to the amount of fatty tissue present at the subject's wrist.

Lastly, in step 568, the scale factor $K_s$ is applied to the raw or uncorrected blood pressure measurement to obtain a scaled or corrected measurement. This is accomplished in the illustrated embodiment by simply multiplying the uncorrected pressure measurement by the scale factor $K_s$. For example, an unscaled value of 100 mmHg and a $K_s$ of 1.2 would result in a corrected pressure value of 120 mmHg. As previously noted with respect to the BMI/PP embodiment described above, the tonometrically measured value will in effect always be less than true intravascular pressure, and accordingly the tonometric value will always be scaled upwards in magnitude.

It will be recognized that while the embodiment of Table 1 above is rendered in terms of a small number (three) of discrete scale index intervals, other numbers of intervals (whether equal in magnitude or not, or companded) may be utilized to impart a greater degree of precision or granularity to the pressure scaling correction process. For example, ten (10) intervals arranged in a logarithmic relationship could be utilized. As yet another alternative, other parameters may be used to qualify or substantiate the scaling process. For example, after the scaling factor $K_s$ is determined using Table 1 (or similar), the proposed scaling factor could be cross-checked against a statistical database for other individuals or sub-classes of individuals (e.g., those with BMI above a certain value). In this fashion, data "outliers" can be identified before the scaling is applied, potentially instigating the caregiver to obtain a confirmatory measurement or consult other resources.

Figure 5I:
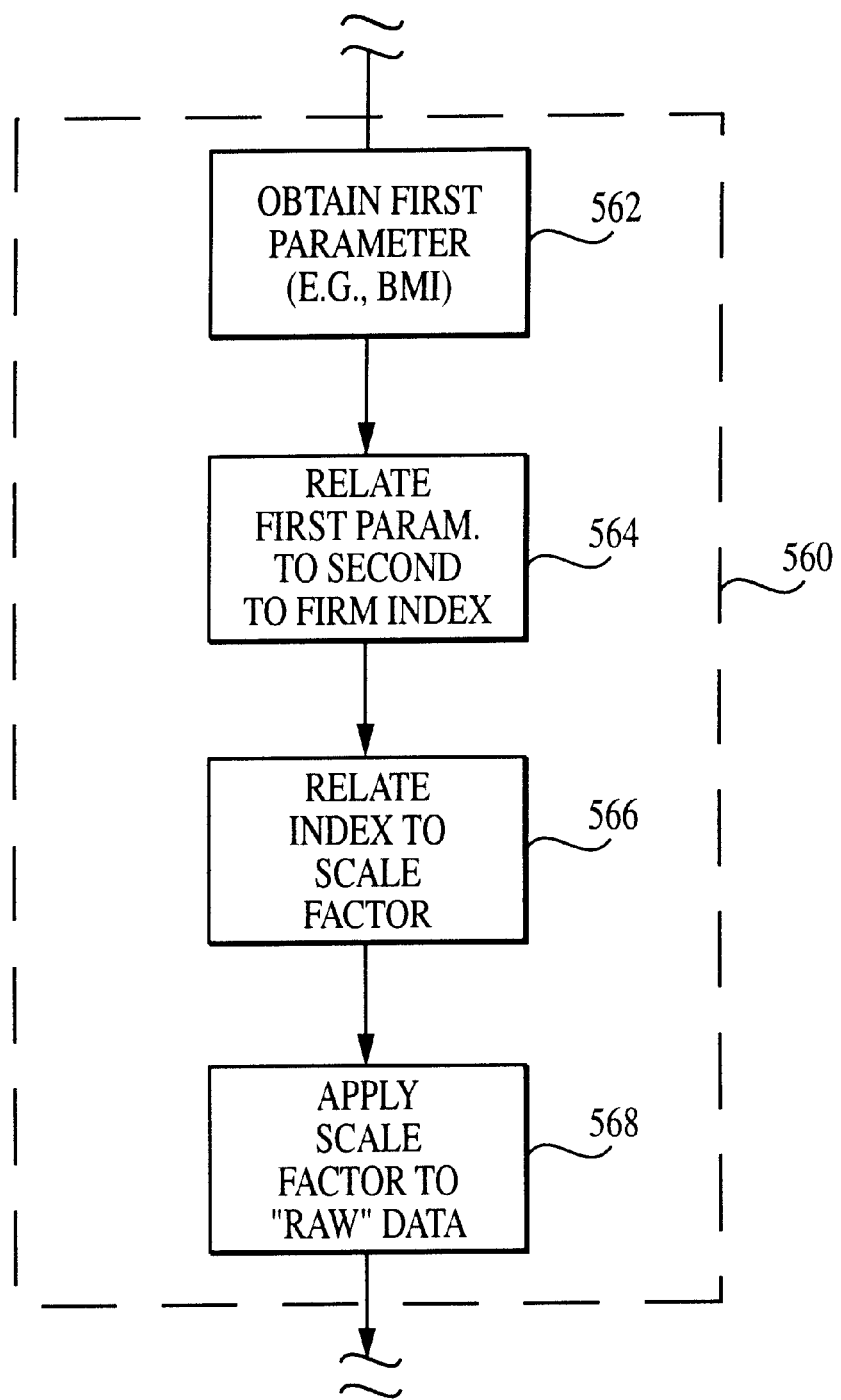
FIG. 5i is a logical flow diagram illustrating a second exemplary embodiment of the method of scaling hemodynamic measurements (using BMI and WC) according to the invention.

Note that since the method of FIG. 5i is at least in the present embodiment somewhat heuristic, very precise measurement of this second parameter is not critical. Accordingly, precise location of the measurement on the subject's wrist is similarly not critical. This underscores a significant advantage of the present methodology, in that the resulting scaling applied to the un-scaled pressure measurement is substantially insensitive to errors in the clinician's or caregiver's wrist circumference measurements. This advantage also exists with respect to the BMI determination of step 1002 previously described, since the BMI determination is fairly insensitive to errors in measurement of the subject's height and/or weight.

Alternatively, other physiological parameters may be utilized to "scale" the waveform (or scaling factor $K_s$ before it is applied to the raw pressure measurement). For example, it is well known that the electrical impedance of a subject's tissue in a given region of the body can be related to the body mass of the subject. Typically, such measurements are made using electrical signals at high frequencies (e.g., 100–200 kHz) so as to overcome noise and other deleterious effects present at lower frequencies. Hence, the present invention may utilize such an electrical impedance measurement obtained from the subject's wrist or arm as a basis for determining body mass (or a BMI-equivalent parameter), the latter being used to scale the tonometric pressure waveform. Such measurements may also be used in a confirmatory capacity to qualify the scale factor derived by other means, and/or provide additional granularity within a given discrete range of scale factor.

Figure 6:
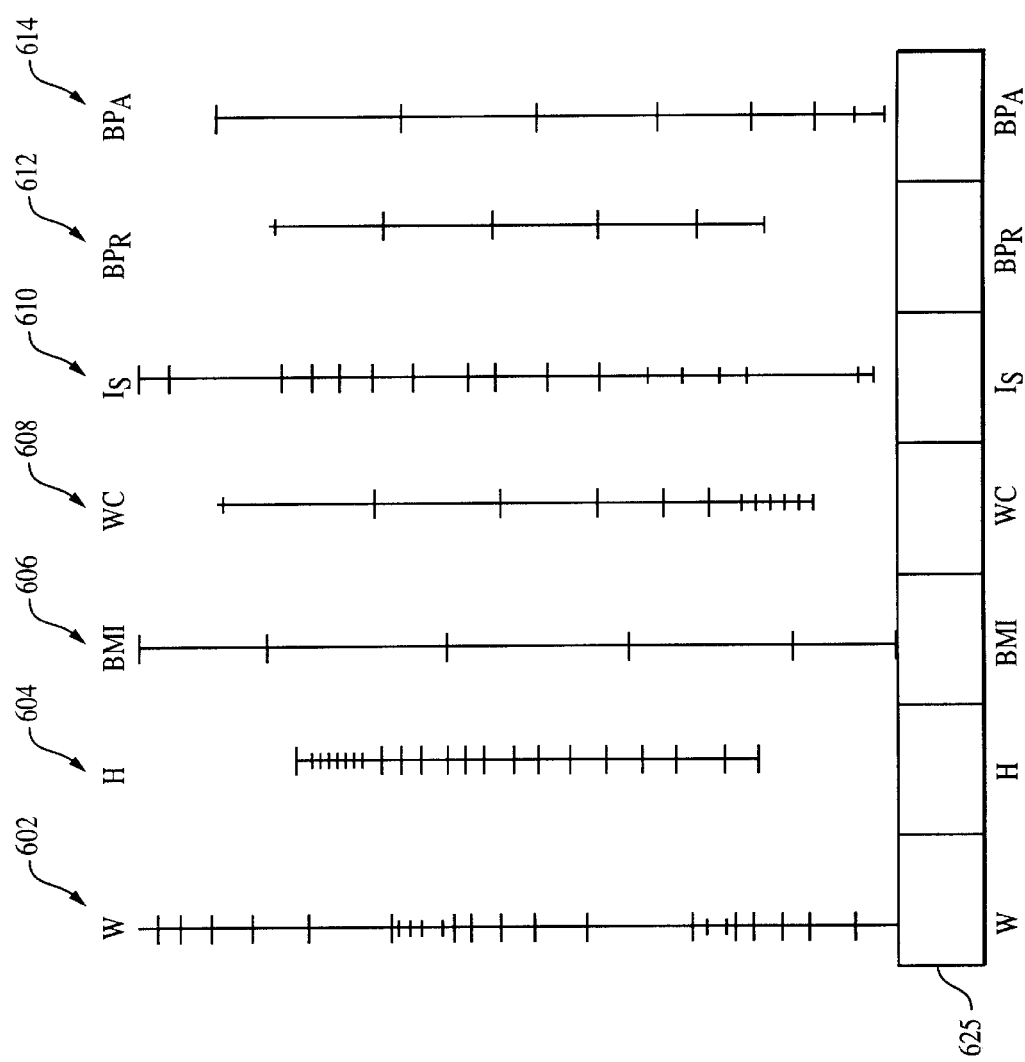
FIG. 6 is a graphical representation of a first embodiment of a nomograph useful for scaling blood pressure measurements according to the methodology of FIG. 5h.

In another embodiment, the relationship between the scale factor $K_s$ and the scale index $I_s$ is determined using a nomograph as illustrated in FIG. 6. As shown in FIG. 6, the nomograph 600 comprises a series of vertical scales 602, 604, 606, 608, 610, 612, 614 which are disposed in parallel relationship to one another on a planar surface (e.g., laminated card, paper, or the like), not shown. In the illustrated embodiment, the vertical scales comprise a weight scale 602, a height scale 604, a BMI scale 606, a wrist circumference (WC) scale 608, a scale index ($I_s$) scale 610, a measured (raw) blood pressure scale 612, and an actual or scaled blood pressure scale 614. The various scales are aligned so as to permit sequential determination of the parameters of interest relating to the scaled blood pressure determination methodology described above. For example, the two left-hand scales 602, 604 are entered (using the data obtained from the subject) and, using a straight-edge such as a ruler, the BMI value determined by aligning the straight-edge to intersect the weight and height scales 602, 604 at the values obtained for each from the subject. The BMI value is then read off of the third (BMI) scale 606 where the straight edge intersects that scale 606. The construction of such nomographic scales is well known in the mathematical arts, and accordingly is not described further herein.

In the nomograph 600 of FIG. 6, the remaining scales (WC, scale factor, measured blood pressure, and corrected blood pressure) are disposed adjacent to the weight, height, and BMI scales to facilitate calculation of the corrected blood pressure. Specifically, after calculating the BMI as previously described, the user simply places the straight-edge on the nomograph such that the edge intersects the BMI and WC scales 606, 608 at the determined BMI value and actual WC value of the subject, respectively. The scale factor $K_s$ is then determined as being the point of intersection of the edge and the scale factor scale 610. Continuing in similar fashion, the user then subsequently aligns the straight-edge such that it intersects the scale factor and raw blood pressure scales 610, 612, thereby intersecting the corrected pressure scale 614 at the value of the true (corrected) blood pressure. Using such scales on the same nomograph 600, the present invention allows the user to "walk" the straight edge across the nomograph 600, thereby obviating the need to record or even remember the results of intermediary calculations. Specifically, for example, after the BMI is calculated, the user simply pivots the straight edge around the point of intersection of the straight edge and the BMI scale 606 until the WC scale 608 is properly intersected, thereby yielding the scale factor. Similarly, the user then pivots the straight edge around the point of intersection of the edge and the scale factor scale 610, and so forth. The user accordingly need never even know the values of BMI or scale factor determined in these intermediary steps; rather, they need only remember (or record) the corrected blood pressure vale from the last scale 614. However, a table 625 for recording the intermediary values (and the initial data obtained from the subject) is optionally provided to facilitate calculation and record keeping. With respect to the latter, the nomograph 600 may be reproduced on a sheet of paper which is layed upon a flat surface. The caregiver simply obtains the weight, height, and WC data from the subject, enters it into the applicable space in the table 625, and then can easily refer to the date when conducting the aforementioned nomographic determinations. After these determinations are mad, the caregiver records the results in the appropriate spaces of the table 625, and then saves the entire sheet in the subject's file or other location. In this fashion, the blood pressure determination can be advantageously reconstructed at a later date, thereby providing accountability and error identification.

It will be appreciated that the foregoing nomograph 600 of FIG. 6 can also be rendered or reduced to a "wheel" calculator configuration of the type well known in the art (not shown). Such wheel comprises one or more stationary and moving wheels, typically fabricated from a flexible laminated material, which rotate around a central spindle. The periphery or surfaces of the wheels are coded such that when various portions of the wheel are aligned (representing various values of the aforementioned parameters), the resulting value can be directly read off of another portion of a wheel. Such devices have the advantage of not requiring use on a flat surface, thereby allowing (i) the user significant mobility, and (ii) pre venting the lack of a flat surface or straight edge from potentially distorting the results of the calculation. Yet other configurations may also be used consistent with the invention.

It will further be appreciated that the scales of the nomograph 600 as described above may be made discrete or continuous in nature, consistent with the desired application of the scaling factors. Hence, the functionality represented in Table 1 above may be readily made in nomographic form, or alternatively, a continuous, non-discrete representation (i.e., with $I_s$ and $K_s$ being continuous variables) may be made with equal ease.

Lastly, it is noted that the nomographic technique described above may also be applied if desired to the BMI/PP method previously described, the calculations of Eqns. 1–5 above being reduced to a nomographic representation by one of ordinary skill in the mathematical arts.

In yet another embodiment of the method of FIG. 5i, the relationship between the scale factor $K_s$ and the scale index $I_s$ is determined algorithmically via an embedded code within the processor or storage device of the blood pressure measurement apparatus (e.g., see discussion relating to FIG. 7 below). For example, the relationships of Table 1 above can be readily reduced to an algorithm or computer program (such as an assembly language program compiled from a C-based source code listing using an assembler) which performs the aforementioned determinations via the digital processor. A look-up table or similar structure can also be coded within the algorithm if desired. This algorithmic embodiment has the distinct advantage of obviating the aforementioned nomograph or similar device, and making the blood pressure correction process transparent to the user. Once properly qualified, the use of software code also reduces the risk of error in the scaling determination, since no misalignment of the straight-edge or similar error can occur. The coding and implementation of such algorithm is readily accomplished by those of ordinary skill in the computer programming arts, and accordingly is not described further herein.

Results of the various intermediary steps (i.e., BMI, scale factor determination) may also be optionally displayed on any display device associated with the system, and stored within the storage device or other desired location (or transmitted to a remote location such as via a computer network) to facilitate additional analysis.

It will further be recognized that the. BMI/PP and BMI/WC methodologies may be combined and/or used in a confirmatory fashion to complement each other. For example, the scaling factor (and/or corrected blood pressure) determined using the aforementioned WC-based technique can be validated or checked using the PP-based technique, or vice versa. Alternatively, the results of the PP and WC-based techniques may be averaged or analyzed statistically. Many such permutations and combinations are possible consistent with the teachings of the present invention.

Lateral Search Methodology

Figure 7:
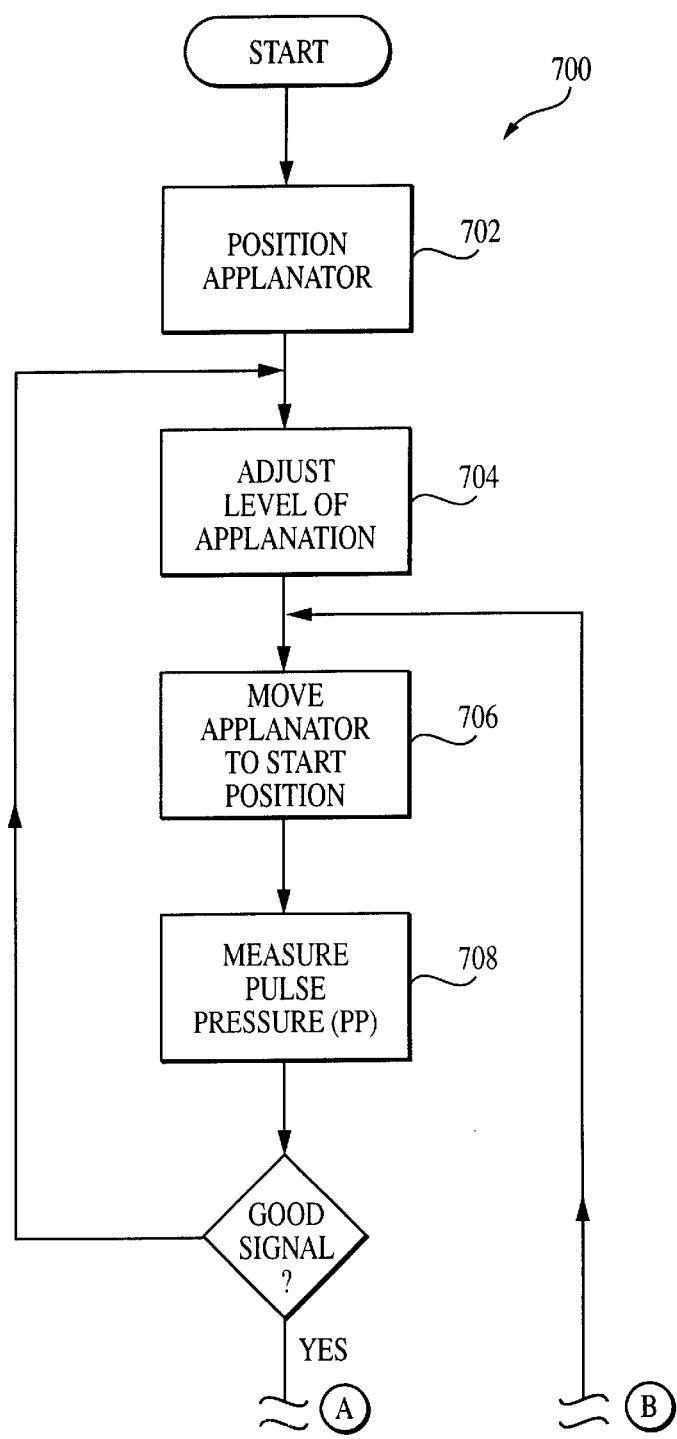
FIG. 7 is logical flow diagram illustrating one exemplary method for laterally positioning the applanation apparatus of FIG. 4 according to the invention.
Figure 7:
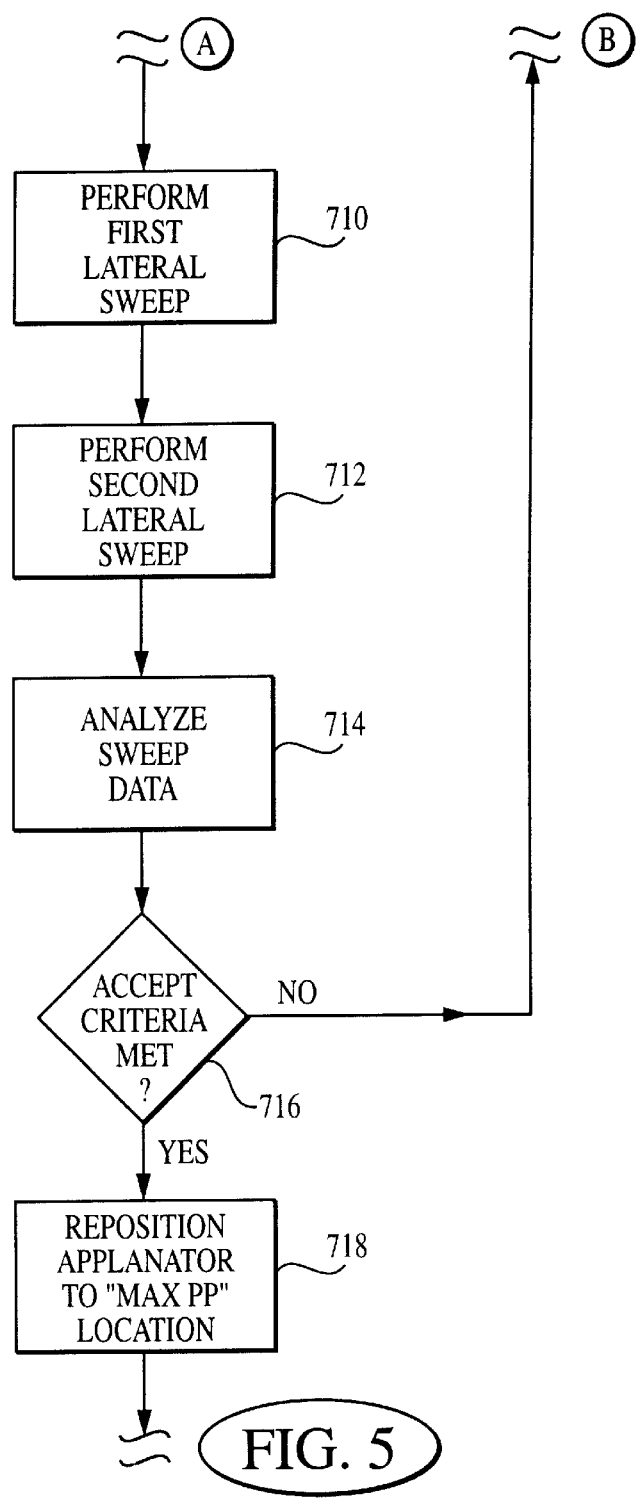

Referring now to FIG. 7, the methodology of lateral positioning of the transducer assembly of the applanator 402 is described. As previously discussed, it is desirable to properly place the transducer 422 directly superior to the blood vessel of concern (e.g., radial artery) prior to performing the optimal applanation, measurement, and scaling procedures discussed above. Such proper lateral placement helps ensure a high level of coupling between the blood vessel wall and transducer face, and in some regards helps to mitigate transfer loss.

As shown in FIG. 7, the exemplary method 700 of the illustrated embodiment comprises first positioning the applanator element 402 (and hence the pressure transducer 422) generally over the blood vessel of interest per step 702 as previously described with respect to FIG. 5. The applanator element 402 is held within a brace or other apparatus such that the former is positioned generally over the inside surface of the subject's wrist. It is noted that the present method anticipates some degree of lateral misalignment.

Next, in step 704, the level of applanation for the applanator 402 is adjusted so as to maintain a substantially constant pressure reading from the transducer 422. This adjustment comprises "servoing" around the designated pressure to as to closely maintain the constant target pressure. This pressure is selected so as to provide adequate signal coupling between the artery wall and the active face of the transducer (via the interposed tissue and coupling layer 423), while also permitting movement of the transducer 422 (and the coupling layer 423) across the surface of the subject's skin without undue friction or distortion of the tissue which might be painful to the subject, or cause anomalies in the measured pressure waveform.

The applanator 402 is then moved laterally across the subject's wrist to a starting position which is offset from the blood vessel of concern (step 706). For example, in one embodiment, the applanator 402 is moved toward the lateral portion of the subject's wrist, more proximate to the radial bone (and specifically the styloid process). It will be recognized, however, that other starting positions (e.g., medial or otherwise) may be used. The applanator 402 is positioned using a lateral positioning stepper motor 845 (see discussion of FIG. 8 below) which is coupled to the applanator 402. However, such positioning may be accomplished using any type of motive force, and may even be performed manually if desired.

Once the applanator 402 is positioned at its starting point, the pulse pressure (PP) is monitored (step 708) based on the systolic and diastolic components obtained from the pressure waveform of the transducer 422.

Next, in step 710, a lateral position sweep is commenced using the lateral positioning motor 845, the latter drawing the applanator 402 (and pressure transducer 422) across the surface of the subject's skin while servoing in the sagittal direction to maintain the aforementioned predetermined pressure. In the present embodiment, a linear position sweep; i.e., constant rate of travel across the surface of the wrist, is utilized, although it will be appreciated that as with the applanation sweep previously described, other profiles (non-linear or otherwise) may be employed. Pulse pressure is measured during the sweep of step 710, and the data stored for analysis.

The sweep rate is selected so as to permit sufficient collection of pressure waveform data and calculation of the PP per unit time, therefore providing the desired level of granularity for PP measurements. Specifically, if the sweep rate is too high, only a few PP data points will be generated, and the lateral position accuracy will be degraded. Conversely, if the sweep rate is too slow, positional localization using PP will be high, but the localization process will be long, thereby extending the time required to ultimately obtain a blood pressure measurement.

Figure 7A:
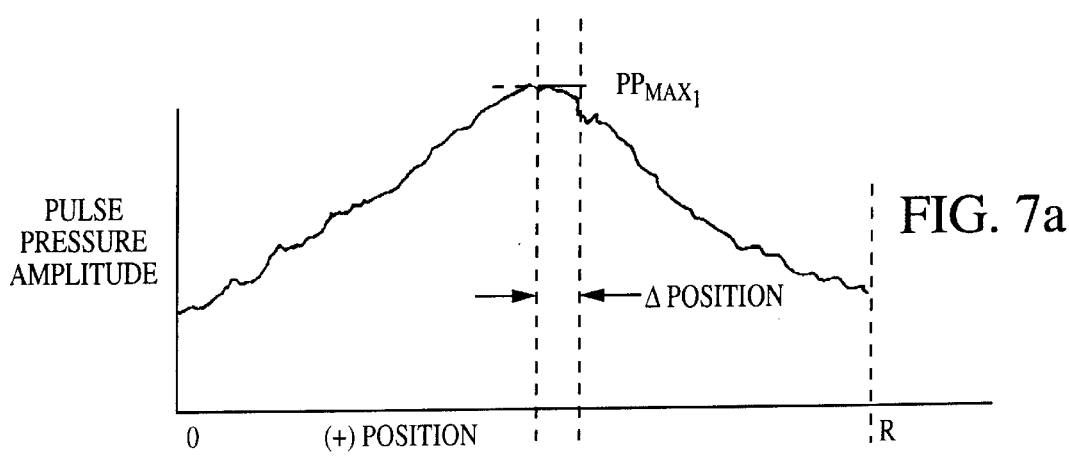
FIGS. 7a–7b are graphs illustrating pulse pressure (PP) versus lateral position for the first and second lateral position sweeps of the method of FIG. 7, including the relative location of the PP maxima therein.

The sweep of step 710 continues until (i) a predetermined position for the applanator 402 relative to the starting position is achieved; and/or (ii) a pulse pressure maximum is observed. Other criteria for terminating the first lateral position sweep may also be utilized. FIG. 7a illustrates an exemplary PP versus lateral position profile obtained using the method 700.

Figure 7B:
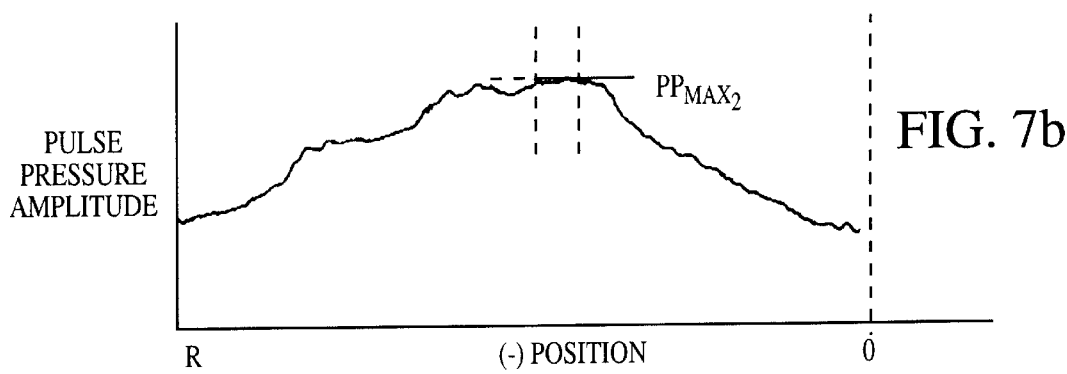

Once the lateral sweep of step 710 is completed, a second lateral sweep in the opposite direction is completed (step 712). As shown in FIG. 7b, this second sweep back-tracks over the first sweep and again records measured PP as a function of time and/or position. In one embodiment, the second sweep operates over a smaller region (i.e., smaller lateral distance) than the first sweep, and at a slower rate to achieve a more precise location for the artery. Similar criteria for terminating the second sweep as to those used in the first sweep (step 710) are employed.

Once the second sweep (step 712) is completed, the data collected for both sweeps is analyzed (step 714) to determine if a true PP maximum has been observed. Specifically, each set of data are analyzed to determine if the maximum PP value occurs at a lateral position (as determined by, e.g., the stepper motor position encoding) corresponding to that for the other sweep, within a prescribed error band. If the PP maxima are well correlated, there is a high confidence that one of the two maxima (or a position there between)

comprises the true position where PP maximum pressure would be measured. Conversely, if the two maxima are not well correlated, additional data gathering (sweeps) may be needed to resolve the ambiguity and/or more accurately localize the desired lateral position for the transducer 422.

Figure 7C:
FIG. 7c is a graph of PP versus lateral position illustrating a spurious artifact (pressure peak) due to motion of the subject during measurement.
Figure 7D:
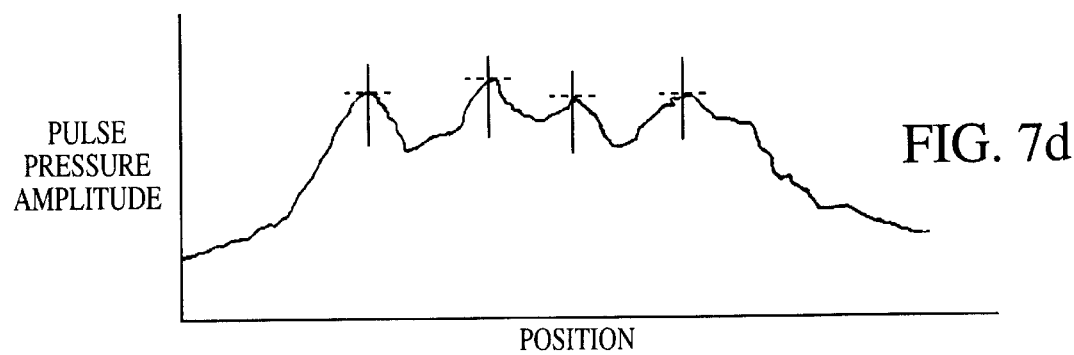
FIG. 7d is a graph of PP versus lateral position illustrating a PP profile having no clear maximum.

In addition to maxima which are not well correlated in position, lateral sweep profiles with multiple local maxima and/or artifacts may be observed. As shown in FIGS. 7c–7d, movement by the subject during sweep or other sources may induce noise within the PP profile(s), thereby frustrating the identification of the true maximum position. In the present embodiment, the occurrence of multiple or no maxima (as determined by, e.g., a mathematical analysis of each interval of the sweep relative to the others) will disqualify a given lateral sweep from consideration, and necessitate additional sweeps (step 716). Signal processing algorithms capable of identifying artifacts and maxima/minima within pressure waveforms are well known in the art, and accordingly are not described further herein.

It is also noted that a "statistical mode" of operation may be employed with respect to the above-described method 700. Specifically, a plurality of lateral position sweeps may be conducted before the analysis of step 714 is performed, with a corresponding (or lesser) number of those sweeps being included in the analyzed data set. In this fashion, artifacts or noise which is present in one sweep may not be present in the next, and therefore will have less degrading effect on the ultimate position determination. Signal processing and/or statistical analysis may be performed to the resulting data as desired.

Furthermore, the method of FIG. 7 (and the apparatus of FIG. 8 below) may be configured so as to localize in an iterative fashion around a calculated position. For example, each lateral positioning sweep is analyzed at its completion, and the results of the maximum location analysis used to localize the spatial region for subsequent sweep(s). Specifically, in one embodiment, the PP data obtained from the first lateral position sweep is analyzed, and the maximum PP location identified. Based on this information, the lateral positioning motor is repositioned (in the direction of motion opposite to the original sweep) to the beginning of a position window centered around the detected maximum PP location. A second, reduced duration "mini-sweep" is then conducted while the PP is measured, and the PP data subsequently analyzed at completion of the mini-sweep to identify the maximum PP location. Correlation analyses such as those previously described herein may or may not be applied as desired, to determine the correlation between the maximum PP locations identified in each sweep. This process may be continued if desired to more accurately locate the maximum PP location. It may also be performed periodically during continuous blood pressure monitoring (i.e., after the optimal applanation level has been determined and any necessary waveform scaling applied, per FIG. 5 above) if desired, so as to account for patient movement, slippage, etc. Specifically, the system may take a lateral positioning "time out", wherein the controller causes the applanation motor 406 to retract the applanator 402 to the predetermined constant pressure level (step 704 of FIG. 7), and one or more lateral update sweeps performed.

It will be recognized that myriad different permutations of the foregoing steps (i.e., compression to a desired level, movement of the applanator 402 laterally across the blood vessel, and analysis of the maxima) may be utilized consistent with the present invention. All such permutations and modifications to this methodology are, given the disclosure provided herein, within possession of those of ordinary skill in the art.

System Apparatus for Hemodynamic Assessment

Figure 8:
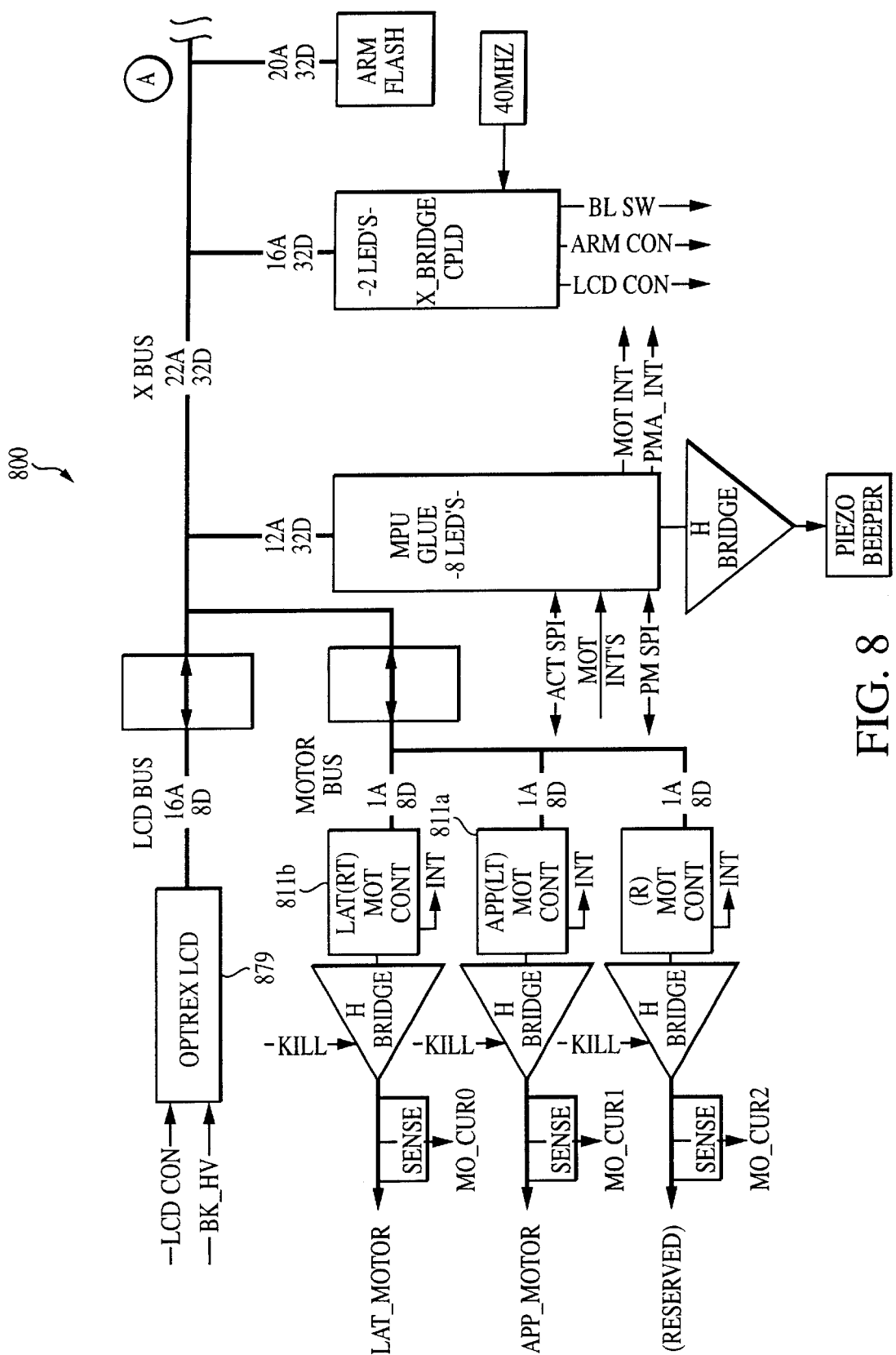
FIG. 8 is a block diagram of one exemplary embodiment of the apparatus for measuring hemodynamic parameters within the blood vessel of a living subject according to the invention.
Figure 8:
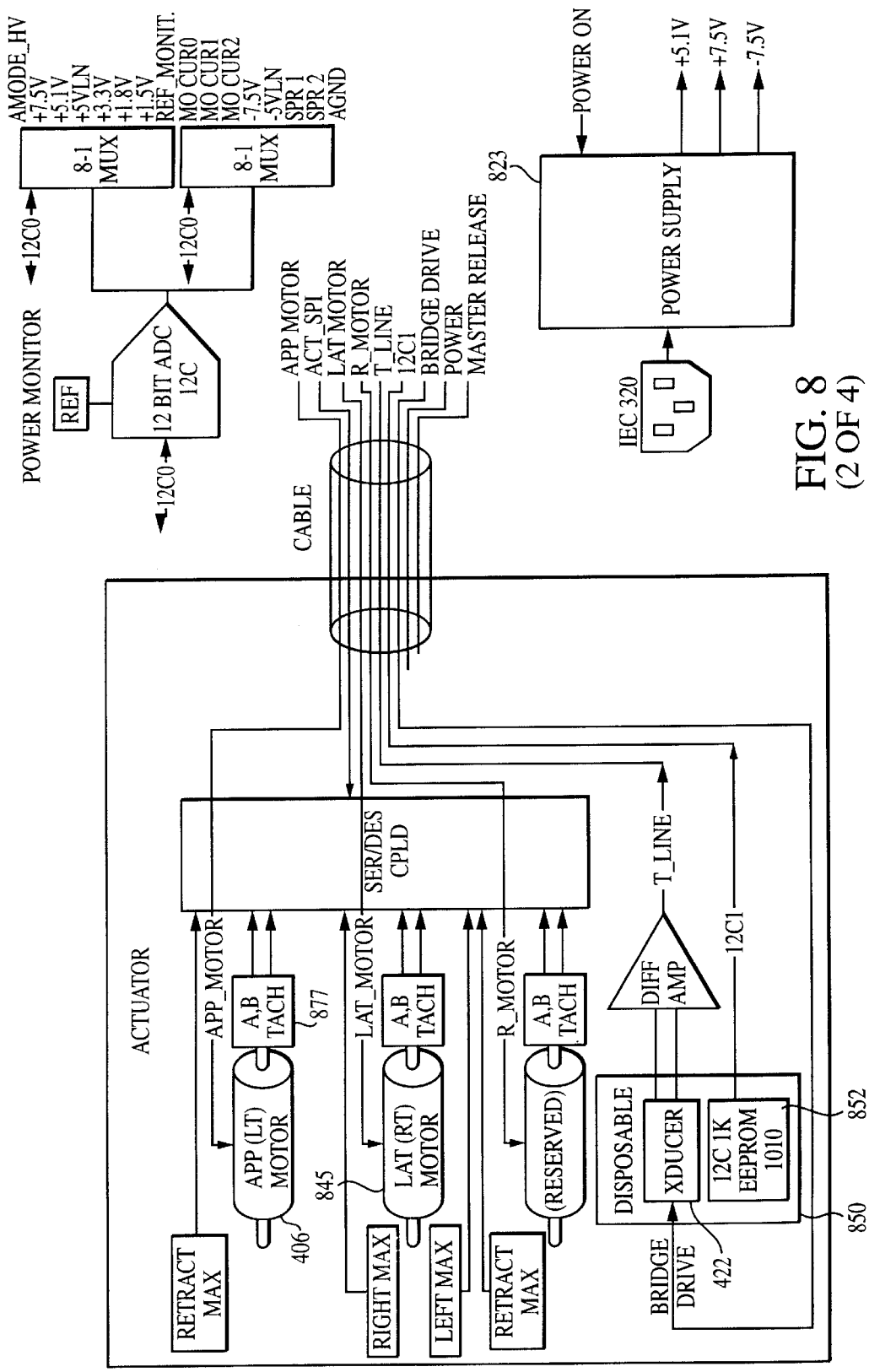
Figure 8:
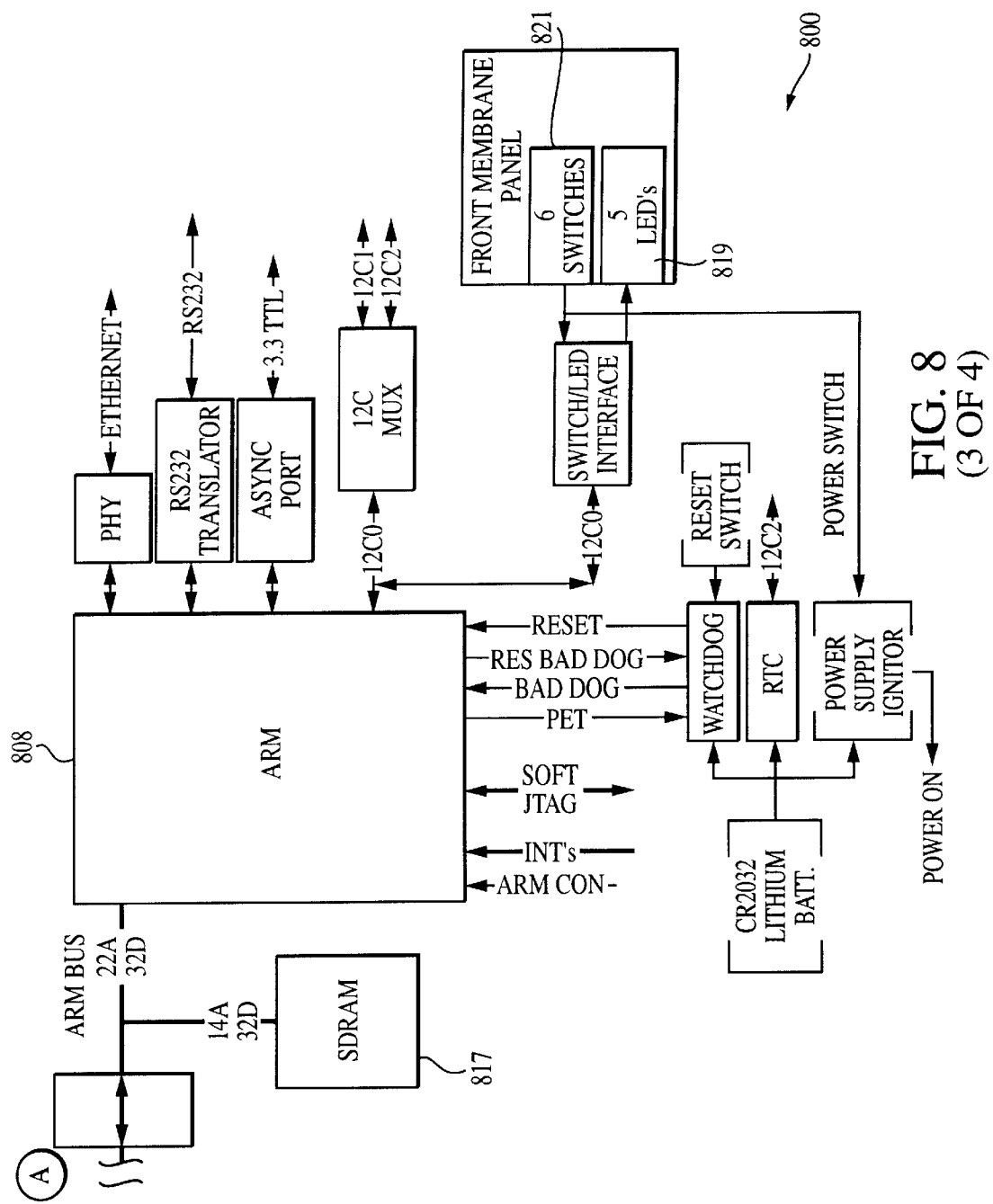
Figure 8:
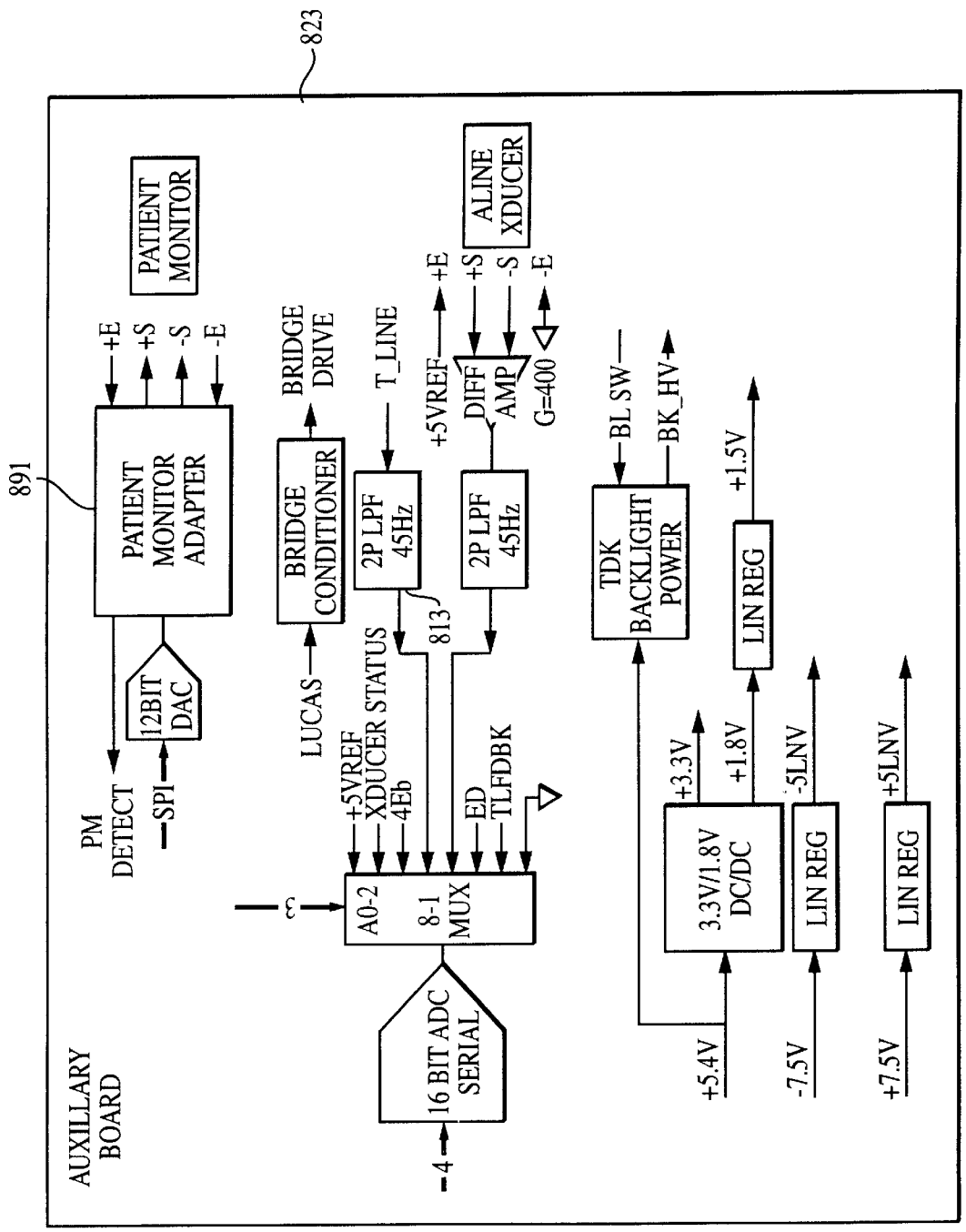

Referring now to FIG. 8, an apparatus for measuring hemodynamic properties within the blood vessel of a living subject is now described. In the illustrated embodiment, the apparatus is adapted for the measurement of blood pressure within the radial artery of a human being, although it will be recognized that other hemodynamic parameters, monitoring sites, and even types of living organism may be utilized in conjunction with the invention in its broadest sense.

The exemplary apparatus 800 of FIG. 8 fundamentally comprises the applanation assembly 400 of FIG. 4 (including element 402 and pressure transducer 422) for measuring blood pressure from the radial artery tonometrically; a digital processor 808 operatively connected to the pressure transducer(s) 422 (and a number of intermediary components) for (i) analyzing the signals generated by the transducer(s); (ii) generating control signals for the stepper motor 406 (via a microcontroller 811a operatively coupled to the stepper motor control circuits); and (iii) storing measured and analyzed data. The motor controllers 811, processor 808, auxiliary board 823, and other components may be housed either locally to the applanator 402, or alternatively in a separate stand-alone housing configuration if desired. The pressure transducer 422 and its associated storage device 852 are optionally made removable from the applanator 402 as described in greater detail below with respect to FIG. 8a.

The pressure transducer 422 is, in the present embodiment, a strain beam transducer element which generates an electrical signal in functional relationship (e.g., proportional) to the pressure applied to its sensing surface 421, although other technologies may be used. The analog pressure signals generated by the pressure transducer 422 are converted into a digital form (using, e.g., an ADC 809) after being optionally low-pass filtered 813 and sent to the signal processor 808 for analysis. Depending on the type of analysis employed, the signal processor 808 utilizes its program (either embedded or stored in an external storage device) to analyze the pressure signals and other related data (e.g., stepper motor position as determined by the position encoder 877, scaling data contained in the transducer's EEPROM 852 via I2C1 signal, etc.).

As shown in FIG. 8, the apparatus 800 is also optionally equipped with a second stepper motor 845 and associated controller 811b, the second motor 845 being adapted to move the applanator assembly 402 laterally across the blood vessel (e.g., radial artery) of the subject as described above with respect to FIG. 7. Operation of the lateral positioning motor 845 and its controller 811b is substantially analogous to that of the applanation motor 406, consistent with the methodology of FIG. 7.

As previously discussed, continuous accurate non-invasive measurements of hemodynamic parameters (e.g., blood pressure) are highly desirable. To this end, the apparatus 800 is designed to (i) identify the proper level of applanation of the subject blood vessel and associated tissue; (ii) continuously "servo" on this condition to maintain the blood vessel/tissue properly biased for the best possible tonometric measurement; and (iii) scale the tonometric measurement as needed to provide an accurate representation of intravascular pressure to the user/operator. During an applantion "sweep", the controller 811a controls the applanation motor 406 to applanate the artery (and interposed tissue) according to a predetermined profile, such as that described with respect to FIG. 5. Similarly, the extension and retraction of the applanation element 402 during the later states of the algorithm (i.e., when the applanation motor 406 is retracted to the optimal applanation position, and subsequent servoing around this point) are controlled using the controller 811a and processor 808. The apparatus 800 is also configured to apply the scaling methodologies previous discussed with respect to FIGS. 5d–5i. Specifically, as discussed with respect to FIG. 5d above, the corrected (scaled) pressure waveform is derived by (i) subtracting the average "n" pulse tonometrically measured mean pressure from each subsequent tonometric sample value of pressure (a "zero mean" sample result); (ii) multiplying each "zero mean" sample value derived in (i) by the derived scale factor, and adding back the "n" beat average mean pressure value; and (iii) repeating the process every "n" beats, using a newly derived scale factor. The resultant waveform is a scaled waveform which is effectively corrected for transfer loss.

In an alternate implementation, a "stretch" calculation is performed according to Eqn. 7 after the applanation sweep and optimization process has been completed:

$$P_{ts}=P_{tu}+(P_{th} \times S_{BMI}) \qquad \text{(Eqn. 7)}$$

Where:

$P_{ts}$="stretched" or corrected tonometric pressure
$P_{tu}$=uncorrected tonometric pressure
$P_{th}$=uncorrected tonometric pressure (high-pass filtered)
$S_{BMI}$=BMI stretch factor This function effectively generates the corrected tonometric pressure data by adding the uncorrected pressure data to a high-pass filtered component of the uncorrected data which has been scaled by the BMI stretch factor. Based on empirical data, the BMI stretch factor in the present embodiment is set to range from between approximately 0.0 to +0.6, although other values may be used.

Note that during an applantion sweep of the "stretch" calculation, the scaling functionality described above is automatically turned off (with auto "on" feature" as well) since no scaling is required during the process of identifying the artifact of concern (e.g., maximum pulse pressure point). Additionally, the user/operator is permitted to determine the minimum cutoff value for the hemodynamic parameter (e.g., pressure) for the applanation sweep. A default value is set at 90 mmHg, although other values may be substituted. This minimum cutoff helps prevent the system from spuriously or erroneously triggering on an invalid event (e.g. a "false" maximum which may result at low pressure values due to the system configuration).

When the apparatus 800 begins data acquisition, a routine is optionally initiated which calculates the coefficients for the system's $4^{th}$-order high pass filter (with a cutoff frequency of 0.1625 Hz, which is selected to eliminate any DC component present in the signal. Additionally, for each data block (i.e., each group of data associated with a given monitoring interval), the apparatus 800 performs a parallel calculation of highpass filter tonometric data for the "stretch" calculation.

The present embodiment also includes a beat detection algorithm. When a new beat is detected (based on processing of the tonometric pressure waveform), a software call is made to update the BMI-determined stretch factor. If the subject's BMI information has not yet been entered, then system simply updates the (pulse) pressure history for future calculations.

The physical apparatus 800 of FIG. 8 comprises, in the illustrated embodiment, a substantially self-contained unit having, inter alia, a combined pressure transducer 422 and applanation device 400, motor controllers 811, RISC digital processor 808 with associated synchronous DRAM (SDRAM) memory 817 and instruction set (including scaling lookup tables), display LEDs 819, front panel input device 821, and power supply 823. In this embodiment, the controllers 811 is used to control the operation of the combined pressure transducer/applanation device, with the control and scaling algorithms are implemented on a continuing basis, based on initial operator/user inputs.

For example, in one embodiment, the user input interface comprises a plurality (e.g., two) buttons disposed on the face of the apparatus housing (not shown) and coupled to the LCD display 879. The processor programming and LCD driver are configured to display interactive prompts via the display 879 to the user upon depression of each of the two buttons. For example, in the present context, one button is assigned as the "weight range" button, wherein when depressed, the LCD display 879 prompts the user to select from one of a plurality of discrete weight ranges. Similarly, the other button is assigned the "height range" function, wherein its depression prompts the user via the display to select one of a plurality of height ranges. Once these two values have been entered, the apparatus 800 automatically determines the PP as previously described, and uses the two inputs to calculate BMI, which is then automatically ratioed to the PP to generate a scaling factor. Such display and control functions are well within the capability of those of ordinary skill in the electronic arts, and accordingly are not described further herein.

Furthermore, a patient monitor (PM) interface circuit 891 shown in FIG. 8 may be used to interface the apparatus 800 to an external or third-party patient monitoring system. Exemplary configurations for such interfaces 891 are described in detail in co-pending U.S. patent application Ser. No. 10/060,646 entitled "Apparatus and Method for Interfacing Time-Variant Signals" filed Jan. 30, 2002, and assigned to the Assignee hereof, which is incorporated by reference herein in its entirety, although other approaches and circuits may be used. The referenced interface circuit has the distinct advantage of automatically interfacing with literally any type of patient monitor system regardless if its configuration. In this fashion, the apparatus 800 of the present invention coupled to the aforementioned interface circuit allows clinicians and other health care professional to plug the apparatus into in situ monitoring equipment already on hand at their facility, thereby obviating the need (and cost) associated with a dedicated monitoring system just for blood pressure measuerment.

Additionally, an EEPROM 852 is physically coupled to the pressure transducer 422 as shown in FIGS. 8 and 8a, so as to form a unitary unit 850 which is removable from the host apparatus 800. The details of the construction and operation of such coupled assemblies are described in detail in co-pending U.S. application Ser. No. 09/652,626, entitled "Smart Physiologic Parameter Sensor and Method", filed Aug. 31, 2000, assigned to the Assignee hereof, and incorporated by reference herein in its entirety.

By using such a coupled and removable arrangement, both the transducer 422 and EEPROM 852 may be readily removed and replaced within the system 800 by the operator. Referring to the scaling methodologies previously described herein (e.g., BMI/PP and BMI/WC), the discrete scaling ranges are advantageously correlated to the unitary assembly 850 such that different assemblies are used for different scaling ranges. For example, in the context of the BMI/WC method as shown best in Table 1 above, three unitary assemblies 850 are provided, one corresponding to each range of scale index $I_s$. The EEPROM 852 of each assembly 850 is accordingly coded with the appropriate scale factor(s) corresponding to that scale index $I_s$, and is also visually coded (e.g., by color). The user/operator selects the appropriate assembly 850 based on the BMI/WC (scale index) value obtained from the subject to be monitored, and inserts the assembly 850 into the apparatus 800. Scaling factors or related data present in the EEPROM 852 are retrieved from the EEPROM, and applied to the unscaled waveform (after applanation level, etc., are optimized as previously described herein) to produce a scaled output. This approach has the benefit of obviating the input or selection of data on the system by the operator; the operator simply determines the scale index value (such as by nomograph or calculator), and then selects the appropriate assembly 750 based on color (or textual information on the assembly or its package).

It will be recognized that the use of a limited number of transducer/EEPROM assemblies may be readily applied to the BMI/PP methodology previously described as well. For example, the full range of BMI/PP can be divided into n=0, 1, 2 . . . discrete intervals (whether linearly or in companded fashion), with a separate assembly 850 for each interval. The EEPROM 852 for each assembly will then contain the scaling data applicable to that interval, such scaling data being for example a scaling function segment, "stretch" factor, or similar. As yet another alternative, the assemblies 850 can be coded based purely on BMI value, thereby alleviating the operator from determining PP and calculating BMI/PP. Numerous other such variants are possible, all considered to fall within the scope of the present invention.

It is also noted that the apparatus 800 described herein may be constructed in a variety of different configurations, and using a variety of different components other than those specifically described herein. The construction and operation of such apparatus (given the disclosure provided herein) are readily within the possession of those of ordinary skill in the medical instrumentation and electronics field, and accordingly not described further herein.

The computer program(s) for implementing the aforementioned methods of hemodynamic assessment using optimal applanation and scaling is/are also included in the apparatus 800. In one exemplary embodiment, the computer program comprises an object ("machine") code representation of a $C^{++}$ source code listing implementing the methodology of FIGS. 5d–5i, either individually or in combination thereof. While $C^{++}$ language is used for the present embodiment, it will be appreciated that other programming languages may be used, including for example VisualBasic™, Fortran, and $C^+$. The object code representation of the source code listing is compiled and may be disposed on a media storage device of the type well known in the computer arts. Such media storage devices can include, without limitation, optical discs, CD ROMs, magnetic floppy disks or "hard" drives, tape drives, or even magnetic bubble memory. The computer program further comprises a graphical user interface (GUI) of the type well known in the programming arts, which is operatively coupled to the display and input device of the host computer or apparatus on which the program is run.

In terms of general structure, the program is comprised of a series of subroutines or algorithms for implementing the applanation and scaling methodologies described herein based on measured parametric data provided to the host apparatus 800. Specifically, the computer program comprises an assembly language/micro-coded instruction set disposed within the embedded storage device, i.e. program memory, of the digital processor or microprocessor associated with the hemodynamic measurement apparatus 800. This latter embodiment provides the advantage of compactness in that it obviates the need for a stand-alone PC or similar hardware to implement the program's functionality. Such compactness is highly desirable in the clinical and home settings, where space (and ease of operation) are at a premium.

Method of Providing Treatment

Figure 9:
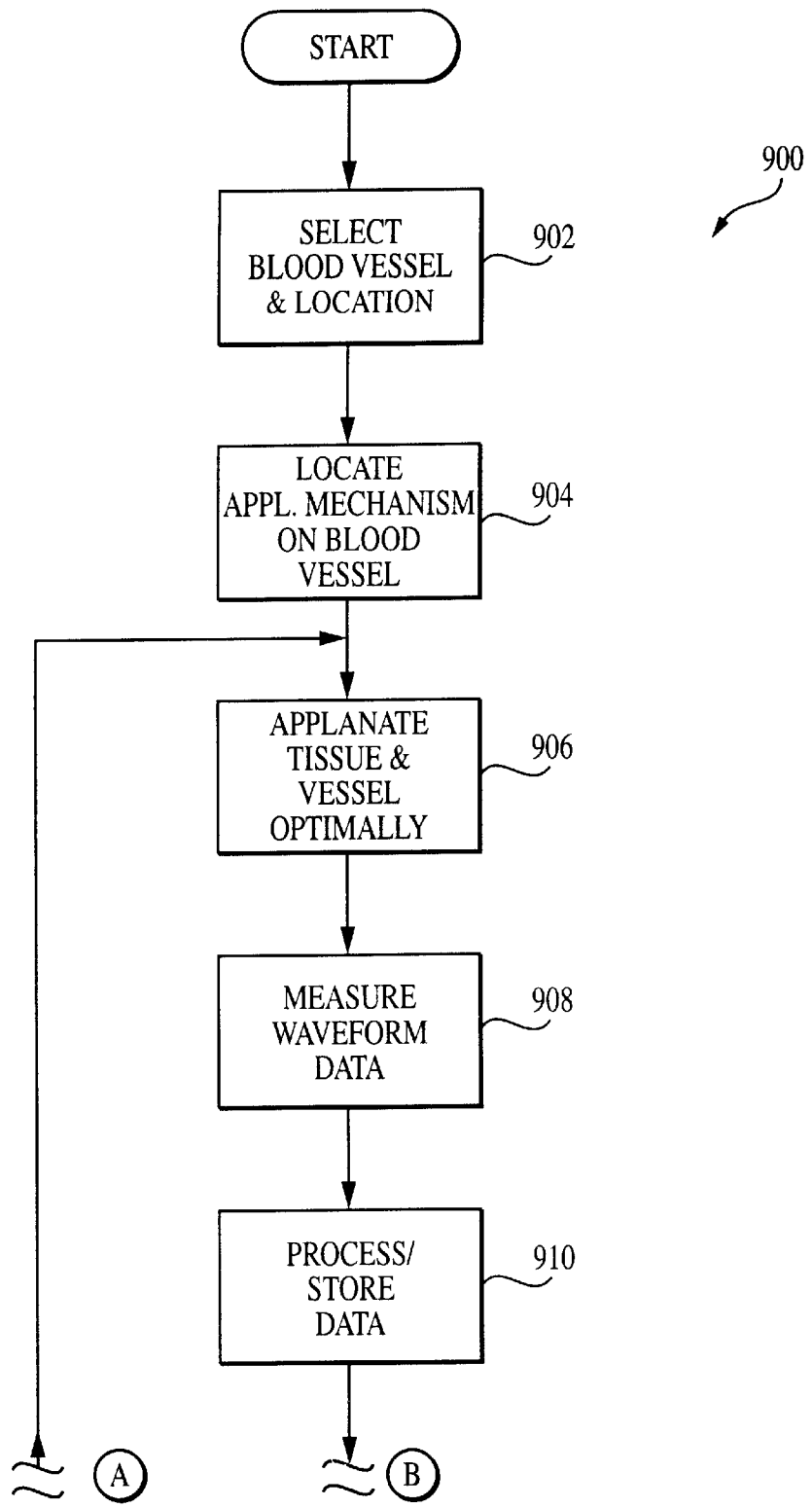
FIG. 9 is a logical flow diagram illustrating one exemplary embodiment of the method of providing treatment to a subject using the aforementioned methods.
Figure 9:
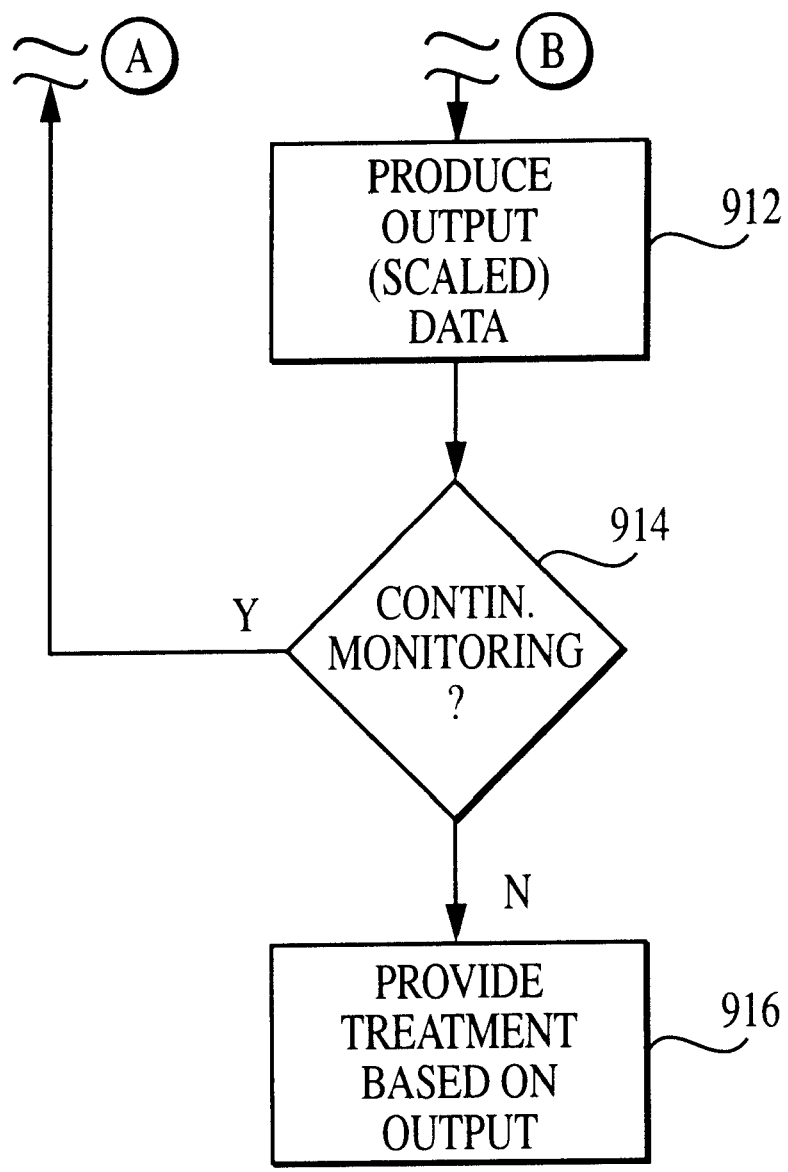

Referring now to FIG. 9, a method of providing treatment to a subject using the aforementioned methods is disclosed. As illustrated in FIG. 9, the first step 902 of the method 900 comprises selecting the blood vessel and location to be monitored. For most human subjects, this will comprise the radial artery (as monitored on the inner portion of the wrist), although other locations may be used in cases where the radial artery is compromised or otherwise not available.

Next, in step 904, the applanation mechanism 400 is placed in the proper location with respect to the subject's blood vessel. Such placement may be accomplished manually, i.e., by the caregiver or subject by visually aligning the transducer and device over the interior portion of the wrist, by the pressure/electronic/acoustic methods of positioning previously referenced, or by other means. Next, the first applanation element 402 is operated per step 906 so as to applanate the tissue surrounding the blood vessel to a desired level so as to identify an optimal position where the effects of transfer loss and other errors associated with the tonometric measurement are mitigated. The prior discussion regarding FIG. 5 herein illustrates one exemplary method of finding this optimum applanation level.

Once the optimal level of applanation for the applanator element 402 is set, the pressure waveform is measured per step 908, and the relevant data processed and stored as required (step 910). Such processing may include, for example, calculation of the pulse pressure (systolic minus diastolic), calculation of mean pressures or mean values over finite time intervals and optional scaling of the measured pressure waveform(s). One or more resulting outputs (e.g., systolic and diastolic pressures, pulse pressure, mean pressure, etc.) Are then generated in step 912 based on the analyses performed in step 910. The relevant portions of the process is then repeated (step 914) if desired so as to provide continuous monitoring and evaluation of the subject's blood pressure.

Lastly, in step 916, the "corrected" measurement of the hemodynamic parameter (e.g., systolic and/or diastolic blood pressure) is used as the basis for providing treatment to the subject. For example, the corrected systolic and diastolic blood pressure values are generated and displayed or otherwise provided to the health care provider in real time, such as during surgery. Alternatively, such measurements may be collected over an extended period of time and analyzed for long term trends in the condition or response of the circulatory system of the subject. Pharmacological agents or other courses of treatment may be prescribed based on the resulting blood pressure measurements, as is well known in the medical arts. Similarly, in that the present invention provides for continuous blood pressure measurement, the effects of such pharmacological agents on the subject's physiology can be monitored in real time.

It is noted that many variations of the methods described above may be utilized consistent with the present invention. Specifically, certain steps are optional and may be performed or deleted as desired. Similarly, other steps (such as additional data sampling, processing, filtration, calibration, or mathematical analysis for example) may be added to the foregoing embodiments. Additionally, the order of performance of certain steps may be permuted, or performed in parallel (or series) if desired. Hence, the foregoing embodiments are merely illustrative of the broader methods of the invention disclosed herein.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A method of tonometrically measuring the pressure in the blood vessel of a living subject, comprising:
   providing a transducer adapted for determining the pressure applied to at least one surface thereof;
   disposing said at least one surface of said transducer proximate to said blood vessel;
   varying the level of compression applied to said blood vessel by said transducer over time;
   determining the level of compression where a desired condition of the pulse pressure associated with said blood vessel exists based on the pressure determined by said transducer;
   maintaining said transducer at or near said level of compression where said desired condition exists;
   measuring at least one pressure value using said transducer during at least a portion of said act of maintaining; and
   scaling said at least one pressure value based on at least the body mass index (BMI) of said subject to produce a corrected value said corrected value being substantially representative of the actual pressure within said blood vessel.

2. A method of measuring the pressure in the blood vessel of a living subject, comprising:
   providing at least one transducer adapted for determining the pressure applied to at least one surface thereof;
   disposing said at least one surface of said at least one transducer proximate to said blood vessel;
   varying the level of compression applied to said blood vessel by said at least one transducer over time;
   determining the level of compression where a desired condition of the pulse pressure associated with said blood vessel exists based on the pressure determined by said at least one transducer;
   maintaining said at least one transducer at or near said level of compression where said desired condition exists; and
   measuring at least one pressure value using said transducer during at least a portion of said act of maintaining.

3. The method of claim 2, wherein said act of disposing comprises disposing said at least one surface of said transducer in contact with the surface of the tissue overlying said at least one blood vessel.

4. The method of claim 2, wherein said act of varying the level of compression comprises performing an applanation sweep from a state of undercompression of said blood vessel to a state of overcompression.

5. The method of claim 4, wherein said applanation sweep comprises linearly varying the position of said transducer with respect to a reference point as a function of time.

6. The method of claim 4, wherein said applanation sweep comprises step-wise varying the position of said transducer with respect to a reference point as a function of time.

7. The method of claim 4, wherein said act of determining the level of compression comprises:
   measuring at least one pressure waveform during said act of performing; and
   identifying at least one artifact within said at least one waveform, said at least one artifact being associated with said desired condition.

8. The method of claim 7, wherein said act of identifying at least one artifact comprises:
   analyzing said at least one waveform on a per-beat basis;
   evaluating at least one parameter associated with a first beat of said at least one waveform;
   evaluating said at least one parameter associated with at least one other beat of said at least one waveform; and
   applying at least one criterion to said beats to identify said desired condition of pulse pressure.

9. The method of claim 8, wherein said at least one parameter comprises the pressure amplitude, and said desired condition comprises maximum pulse pressure.

10. The method of claim 9, wherein said at least one other beat comprises two consecutive beats, said two consecutive beats being sequential with said first beat, said criterion comprising a difference in the pressure amplitude of a predetermined percentage.

11. The method of claim 2, further comprising:
    determining a first physiologic parameter of said subject;
    determining a second physiologic parameter of said subject;
    forming a relationship between said first and second parameters; and
    using said relationship to scale said at least one pressure value.

12. The method of claim 11, wherein said first physiologic parameter comprises the body mass index (BMI) of said subject.

13. The method of claim 12, wherein said second physiologic parameter comprises the pulse pressure measured from said subject.

14. The method of claim 13, wherein said act of forming comprises forming a ratio of said BMI to said PP.

15. The method of claim 14, wherein said act of using comprises (i) correlating said ratio to a scale factor; and (ii) multiplying said at least one pressure value by said scale factor.

16. The method of claim 12, wherein said second physiologic parameter comprises the circumference of said subject's wrist (WC).

17. The method of claim 16, wherein said act of forming comprises forming a ratio of said BMI to said WC.

18. The method of claim 2, wherein said act of varying the level of compression over time comprises varying the level of compression at a rate which is at least in part a function of the heart rate of said subject.

19. The method of claim 2, further comprising:
    determining at least one physiologic parameter of said subject;
    identifying a relationship between said at least one parameter and a scaling factor for said at least one pressure value measured from said blood vessel; and
    using said scaling factor to scale said at least one pressure value.

20. The method of claim 19, wherein said at least one parameter comprises body fat content.

21. The method of claim 19, further comprising determining a mean pressure within said at least one waveform; and wherein said act of using said scaling factor to scale said at least one pressure value comprises applying said scaling factor to pressure values above and below said mean.

22. The method of claim 21, wherein said act of applying scaling factors to pressure values above and below said mean comprises applying a positive (+) scaling factor to systolic pressures above said mean, and a negative (−) scaling factor to diastolic pressures below said mean.

23. The method of claim 2, further comprising varying the position of said at least one transducer in a substantially lateral direction relative to said blood vessel so as to optimize said desired condition of said act of determining.

24. The method of claim 23, further comprising varying the position of said at least one transducer in a substantially proximal direction relative to said blood vessel so as to optimize said desired condition of said act of determining.

25. The method of claim 24, wherein said desired condition comprises maximum pulse pressure, and at least one of said acts of varying comprises:

measuring at least one pressure waveform during said act of varying;

varying the position of said at least one transducer over a range of positions; and identifying that position where said pulse pressure is maximized for a given level of compression.

26. An apparatus for measuring the pressure within the blood vessel of a living subject comprising:

a pressure transducer adapted to detect the pressure associated with said blood vessel and generate a signal relating thereto;

at least one storage device associated with said pressure transducer, said at least one storage device having scaling data stored therein;

at least one applanation assembly adapted to bias a portion of tissue proximate to said blood vessel;

a controller operatively coupled to said at least one applanation assembly and adapted to control the position thereof; and a processor operatively connected to said transducer, at least one storage device, and said controller, said processor configured to generate an estimate of said blood pressure within said vessel based at least in part on said signal and said scaling data.

27. The apparatus of claim 26, wherein said blood vessel comprises the radial artery of a human being, and said portion of tissue is disposed on the wrist of said subject.

28. The apparatus of claim 26, wherein said pressure transducer is physically coupled to said at least one applanation assembly, and comprises at least one active surface which contacts said portion of said tissue, said portion of tissue at least partly overlying said blood vessel.

29. The apparatus of claim 26, wherein said controller and processor comprise a single integrated circuit (IC) device.

30. The apparatus of claim 26, further comprising at least one computer program adapted to control the level of bias applied to said portion of tissue.

31. The apparatus of claim 30, wherein said at least one computer program is further adapted to maintain said bias level such that the pulse pressure associated with said blood vessel is substantially maximized.

32. The apparatus of claim 26, wherein said scaling data is selected based at least in part on at least one physical parameter associated with said living subject.

33. The apparatus of claim 32, wherein said at least one physical parameter comprises the body mass index of said subject.

34. The apparatus of claim 32, wherein said at least one physical parameter comprises an index based at least in part on the wrist circumference of said subject.

35. The apparatus of claim 26, wherein said pressure transducer and said at least one storage device comprise a substantially unitary assembly adapted for removal from said apparatus.

36. The apparatus of claim 35, wherein said at least one storage device contains scaling data adapted for use on a subject having a physical parameter falling within a predetermined range.

37. The apparatus of claim 36, wherein said physical parameter comprises a body mass index.

38. The apparatus of claim 36, wherein said physical parameter comprises body fat content.

39. The apparatus of claim 36, wherein said unitary assembly is visibly coded to identify the range of said physical parameter for which it may be used.

40. The apparatus of claim 39, wherein said visible coding comprises color coding, with the unitary assembly associated with each range having a different color.

41. The apparatus of claim 26, wherein said storage device contains a plurality of scaling data, and the scaling data retrieved from said storage device and applied to a given subject is selected based on the measurement of at least one physical parameter obtained from said subject and provided to said apparatus.

42. The apparatus of claim 41, wherein said act of providing comprises entering said measurement(s) into said apparatus using an input device.

43. An information storage device, comprising:

a data storage medium;

a plurality of data stored on said medium, said plurality of data comprising a computer program adapted to run on a data processor, said data processor being operatively coupled to a controller which controls the position of a pressure transducer, said computer program, processor and controller being configured for determining the blood pressure of a living subject using the method comprising:

varying the level of compression applied to said blood vessel by at least one pressure transducer over time;

determining the level of compression where a desired condition of the pulse pressure associated with said blood vessel exists based on the pressure determined by said at least one transducer;

maintaining said at least one transducer at or near said level of compression where said desired condition exists; and measuring at least one pressure value using said transducer during at least a portion of said act of maintaining.

* * * * *

UNITED STATES PATENT AND TRADEMARK OFFICE
CERTIFICATE OF CORRECTION

PATENT NO. : 6,730,038 B2
DATED : May 4, 2004
INVENTOR(S) : Stuart L. Gallant et al.

It is certified that error appears in the above-identified patent and that said Letters Patent is hereby corrected as shown below:

<u>Title page,</u>
Item [75], Inventors, should read -- Stuart L. Gallant, San Diego, CA (US); Gregory I. Voss, Solana Beach, CA (US); and William H. Markle, Laguna Niguel, CA (US) --

<u>Column 31,</u>
Lines 33-37, should read -- scaling said at least one pressure value based on at least the body mass index (BMI) of said subject to produce a corrected value, said corrected value being substantially representative of the actual pressure within said blood vessel. --

Signed and Sealed this

Twenty-seventh Day of July, 2004

JON W. DUDAS
*Acting Director of the United States Patent and Trademark Office*